US012740688B2

(12) United States Patent
Harada

(10) Patent No.: US 12,740,688 B2
(45) Date of Patent: Sep. 22, 2026

(54) ENDOSCOPE AND TREATMENT TOOL ELEVATING MECHANISM

(71) Applicant: FUJIFILM Corporation, Tokyo (JP)

(72) Inventor: Takashi Harada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 557 days.

(21) Appl. No.: 18/069,437

(22) Filed: Dec. 21, 2022

(65) Prior Publication Data

US 2023/0122213 A1 Apr. 20, 2023

Related U.S. Application Data

(63) Continuation of application No. PCT/JP2021/026098, filed on Jul. 12, 2021.

(30) Foreign Application Priority Data

Jul. 17, 2020 (JP) ................................ 2020-122665

(51) Int. Cl.
*A61B 1/00* (2006.01)
*A61B 1/018* (2006.01)
(Continued)

(52) U.S. Cl.
CPC ...... *A61B 1/00098* (2013.01); *A61B 1/00101* (2013.01); *A61B 1/00128* (2013.01);
(Continued)

(58) Field of Classification Search
CPC ............ A61B 1/00098; A61B 1/00101; A61B 1/00135; A61B 1/00142; A61B 1/00154;
(Continued)

(56) References Cited

U.S. PATENT DOCUMENTS 5,460,167 A * 10/1995 Yabe .................. A61B 1/00174 600/107
5,460,168 A * 10/1995 Masubuchi ........ A61B 1/00098 600/107
(Continued)

FOREIGN PATENT DOCUMENTS

CN 110461243 A 11/2019
JP 3-90126 A 4/1991
(Continued)

OTHER PUBLICATIONS

Japanese Office Action for counterpart Japanese Application No. 2022-536340, dated Aug. 21, 2024, with English translation.
(Continued)

*Primary Examiner* — Ryan N Henderson
(74) *Attorney, Agent, or Firm* — Birch, Stewart, Kolasch & Birch, LLP

(57) ABSTRACT

There are provided an endoscope and a treatment tool elevating mechanism capable of achieving improvement in accessibility of a cleaning brush, prevention of wear of a distal-end-portion main body, and prevention of slipping of a treatment tool into the lower side of an operating wire. When viewed in a second direction perpendicular to both the longitudinal axis of the distal-end-portion main body and a first direction perpendicular to the longitudinal axis, a wire distal end portion of the operating wire connected to a wire connection portion of a treatment tool elevator is positioned on the other direction side with respect to an elevator main body portion of the treatment tool elevator. A second wall portion of an elevator-housing-space forming member has a first wall surface at least a portion of which has a shape along the trajectory of the wire connection portion that rotates about a rotary shaft, and a second wall surface provided at a position on one direction side of the first direction with respect to the first wall surface and having a shape extending
(Continued)

along the trajectory of the elevator main body portion that rotates about the rotary shaft. When viewed in the second direction, the second wall surface overlaps at least a portion of the wire distal end portion in the first direction.

13 Claims, 17 Drawing Sheets

(51) Int. Cl.
*A61B 8/00* (2006.01)
*A61B 8/12* (2006.01)

(52) U.S. Cl.
CPC .......... *A61B 1/00137* (2013.01); *A61B 1/018* (2013.01); *A61B 8/12* (2013.01); *A61B 8/445* (2013.01)

(58) Field of Classification Search
CPC ... A61B 1/00137; A61B 1/018; A61B 1/0008; A61B 1/00087
See application file for complete search history.

(56) References Cited

U.S. PATENT DOCUMENTS

| | | | | |
|---|---|---|---|---|
| 7,491,166 | B2 * | 2/2009 | Ueno | A61B 1/018 600/129 |
| 8,435,170 | B2 * | 5/2013 | Wood | A61B 1/018 600/129 |
| 2017/0020370 | A1 * | 1/2017 | Yamaya | A61B 1/00142 |
| 2018/0206708 | A1 * | 7/2018 | Miller | A61B 1/00098 |
| 2020/0008778 | A1 | 1/2020 | Morimoto et al. | |
| 2020/0397233 | A1 * | 12/2020 | Hosogoe | A61B 1/00148 |
| 2021/0059507 | A1 * | 3/2021 | Yamaya | A61B 1/018 |
| 2021/0068628 | A1 * | 3/2021 | Yamaya | A61B 1/0057 |
| 2021/0076909 | A1 * | 3/2021 | Ueda | A61B 1/0014 |
| 2021/0290042 | A1 * | 9/2021 | Hosogoe | A61B 1/00101 |
| 2022/0202281 | A1 * | 6/2022 | Hosogoe | A61B 1/00098 |

FOREIGN PATENT DOCUMENTS

| | | | |
|---|---|---|---|
| JP | 5-56913 | A | 3/1993 |
| JP | 6-315458 | A | 11/1994 |
| JP | 7-194513 | A | 8/1995 |
| JP | 8-154890 | A | 6/1996 |
| JP | 11-299728 | A | 11/1999 |
| JP | 2604553 | Y2 | 5/2000 |
| JP | 2007-215634 | A | 8/2007 |
| JP | 2019-531145 | A | 10/2019 |
| WO | WO 2016/027574 | A1 | 2/2016 |

OTHER PUBLICATIONS

International Preliminary Report on Patentablity (PCT/IPEA/409) dated Apr. 28, 2022 with an English translation.
International Search Report (PCT/ISA/210) dated Sep. 28, 2021 for Application No. PCT/JP2021/026098 with an English translation.
Written Opinion of the International Searching Authority (PCT/ISA/237) dated Sep. 28, 2021 for Application No. PCT/JP2021/026098.
Japanese Office Action for counterpart Japanese Application No. 2022-536340, dated Mar. 21, 2024, with English translation.
Chinese Office Action and Search Report for counterpart Chinese Application No. 202180045165.9, dated Nov. 11, 2025, with English translation.
Chinese Office Action for counterpart Chinese Application No. 202180045165.9, dated Jan. 27, 2026, with English translation.
Chinese Office Action and Search Report for counterpart Chinese Application No. 202180045165.9, dated Jul. 16, 2025, with English translation.
Chinese Rejection Decision for counterpart Chinese Application No. 202180045165.9, dated Apr. 11, 2026, with English translation.

* cited by examiner 30
28
24
26
Ax
18
16
15
12
14
54
50
15A
22
48
64
62
62
57
52
59
10
20
46
X(−)
Y(+)
Z(+)
Z(−)
X(+)
Y(−)

300
24
76
304b
304
74
304a
314
315
312
74
58
310
308
328
322
329
321
325
38
324
320
36
318
323
306
302
X(−)
Y(−)
Z(+)
Z(−)
X(+)
Y(+)

ENDOSCOPE AND TREATMENT TOOL ELEVATING MECHANISM

CROSS-REFERENCE TO RELATED APPLICATIONS

The present application is a Continuation of PCT International Application No. PCT/JP2021/026098 filed on Jul. 12, 2021 claiming priority under 35 U.S.C. § 119(a) to Japanese Patent Application No. 2020-122665 filed on Jul. 17, 2020. Each of the above applications is hereby expressly incorporated by reference, in its entirety, into the present application.

BACKGROUND OF THE INVENTION

1. Field of the Invention

The present invention relates to an endoscope including, at a distal end side of an insertion section, a treatment tool elevator that changes the lead-out direction of a treatment tool, and a treatment tool elevating mechanism.

2. Description of the Related Art

Various types of treatment tools are led in through a treatment tool lead-in port provided at an operation section in an endoscope, and the treatment tools are led out to be used for treatment to the outside through a treatment tool lead-out port that opens at a distal end portion of an insertion section. For example, a treatment tool such as a guide wire or a contrast tube is used in a duodenoscope. A treatment tool such as a puncture needle is used in an ultrasonic endoscope. A treatment tool such as forceps or a snare is used in the other scopes such as a direct-viewing scope and an oblique-viewing scope. To treat a desired site in a subject, it is necessary to change the lead-out direction of such a treatment tool at a tip portion thereof. Therefore, the distal end portion of the insertion section is provided with a treatment tool elevating mechanism that changes the lead-out direction of a treatment tool (JP2019-531145A). The treatment tool elevating mechanism has a treatment tool elevator and changes the orientation of the treatment tool elevator between an elevated position and a lying position.

As the treatment tool elevating mechanism, a mechanism of a wire pulling method (open type) in which the distal end of an operating wire is directly attached to an elevator and in which the proximal end of the operating wire is connected to an operation lever provided at an operation section is known (refer to JP2604553Y, JP-H05-56913, and JP-H06-315458). The mechanism rotates the elevator around a rotational axis by pushing and pulling the operating wire by the operation lever, and thereby changes the orientation of the elevator between the elevated position and the lying position.

In such a mechanism of the wire pulling method, the operating wire is exposed inside an elevator housing space that houses the treatment tool elevator. Thus, there is a likelihood of a treatment tool slipping into the lower side of the operating wire.

Here, JP-H08-154890 discloses an endoscope including a treatment tool elevator, an operating wire fixed to a side portion of the treatment tool elevator, and a distal-end-portion main body including a pair of side walls constituting an elevator housing space that houses the treatment tool elevator. Of the pair of side walls of the distal-end-portion main body described in JP-H08-154890, the side wall (hereinafter referred to as the facing side wall) facing the side portion of the treatment tool elevator described above has a shape that fills a gap on the lower side of the operating wire. The facing side wall prevents a treatment tool from slipping into the lower side of the operating wire.

SUMMARY OF THE INVENTION

Meanwhile, since the facing side wall is provided so as to fill the gap on the lower side of the operating wire in the endoscope described in JP-H08-154890, a space (elevator housing space) between the pair of side walls of the distal-end-portion main body is narrowed and degrades accessibility of a cleaning brush with respect to the space between the pair of side walls. In addition, when the treatment tool elevator is displaced between the elevated position and the lying position via the operating wire, the operating wire may come into sliding-contact with the upper surface of the facing side wall. As a result, the facing side wall of the distal-end-portion main body may be worn due to repeated displacement of the treatment tool elevator.

The present invention has been made in consideration of such circumstances, and an object of the present invention is to provide an endoscope and a treatment tool elevating mechanism capable of achieving improvement in accessibility of a cleaning brush, prevention of wear of a distal-end-portion main body, and prevention of slipping of a treatment tool into the lower side of an operating wire.

An endoscope for achieving an object of the present invention includes an operation section at which an operating member is provided; an insertion section that is provided on the distal end side of the operation section and that is to be inserted into a subject; a distal-end-portion main body that is positioned at the distal end of the insertion section; an elevator-housing-space forming member that is detachably attached to the distal-end-portion main body and that forms an elevator housing space; a proximal end wall portion that is provided at the distal-end-portion main body or the elevator-housing-space forming member and at which a lead-out port for a treatment tool opens; a first wall portion that extends from the proximal end wall portion to the distal end side of the distal-end-portion main body, the first wall portion being provided at a position on one direction side of a first direction perpendicular to the longitudinal axis of the distal-end-portion main body with respect to the lead-out port; a second wall portion that is provided at the elevator-housing-space forming member and that forms, together with the proximal end wall portion and the first wall portion, the elevator housing space, the second wall portion facing the first wall portion at a position on the other direction side opposite to the one direction side with respect to the lead-out port; a treatment tool elevator that is disposed in the elevator housing space and that is rotatable between a lying position and an elevated position about a rotary shaft parallel to the first direction, the treatment tool elevator having an elevator main body portion rotatably held by the rotary shaft, an elevator distal end portion provided on the distal end side of the elevator main body portion, and a wire connection portion provided at the elevator distal end portion; and an operating wire that is connected to the wire connection portion and that rotates the treatment tool elevator. When viewed in a second direction perpendicular to both the longitudinal axis and the first direction, a wire distal end portion of the operating wire connected to the wire connection portion is positioned on the other direction side with respect to the elevator main body portion. The second wall portion has a first wall surface at least a portion of which has a shape along the trajectory of the wire connection portion that rotates about the rotary shaft, and a second wall surface that is provided at a position on the one direction side with respect to the first wall surface and that has a shape extending along the trajectory of the elevator main body portion that rotates about the rotary shaft. The second wall surface overlaps at least a portion of the wire distal end portion in the first direction when viewed in the second direction.

According to the endoscope, a treatment tool can be prevented, by the second wall surface, from slipping into the lower side of the wire distal end portion of the operating wire.

In the endoscope according to another aspect of the present invention, the wire distal end portion has a shape projecting further from the elevator distal end portion on the other direction side than the elevator main body portion.

In the endoscope according to another aspect of the present invention, the second wall surface is provided at a position on one direction side with respect to the center axis of the wire distal end portion when viewed in the second direction. Consequently, it is possible to reliably prevent a treatment tool from slipping into the lower side of the wire distal end portion of the operating wire.

In the endoscope according to another aspect of the present invention, the second wall portion has a step surface formed between the first wall surface and the second wall surface. The step surface has a shape extending along the trajectory of the wire distal end portion that rotates about the rotary shaft. Consequently, it is possible to prevent a treatment tool from slipping into the lower side of the wire distal end portion of the operating wire.

In the endoscope according to another aspect of the present invention, the step surface has an arc shape when viewed in the first direction. Consequently, it is possible to prevent a treatment tool from slipping into the lower side of the wire distal end portion of the operating wire.

In the endoscope according to another aspect of the present invention, the first wall surface is provided on the other direction side with respect to the operating wire when viewed in the second direction. Consequently, it is possible to increase the thickness of the elevator distal end portion.

In the endoscope according to another aspect of the present invention, the distal-end-portion main body has the proximal end wall portion and the first wall portion, and the elevator-housing-space forming member is a cap having the second wall portion.

In the endoscope according to another aspect of the present invention, an opening window that exposes the elevator housing space when viewed from the distal end side of the cap is formed at a distal end portion of the cap. Consequently, it is possible to insert fingers or a tool into the elevator housing space through the opening window at the time of attaching and detaching of the cap with respect to the distal-end-portion main body, in particular, at the time of detaching thereof. It is thus possible to attach and detach the cap easily. In addition, the opening window can be used in formation of the step surface using a metal mold.

In the endoscope according to another aspect of the present invention, the elevator-housing-space forming member has the proximal end wall portion, the first wall portion, and the second wall portion, and the endoscope includes an ultrasonic transducer provided on the distal end side of the distal-end-portion main body.

In the endoscope according to another aspect of the present invention, the endoscope includes an insert molded body in which the treatment tool elevator and the operating wire are integrated with each other.

In the endoscope according to another aspect of the present invention, the treatment tool elevator and the operating wire are formed as separate bodies.

A treatment tool elevating mechanism for achieving an object of the present invention is a treatment tool elevating mechanism that is to be attached to a distal-end portion main body of an endoscope and that changes the lead-out direction of a treatment tool. The endoscope includes an operation section at which an operating member is provided, an insertion section that is provided on the distal end side of the operation section and that is to be inserted into a subject, and a distal-end-portion main body that is positioned at the distal end of the insertion section. The treatment tool elevating mechanism includes an elevator-housing-space forming member that is detachably attached to the distal-end-portion main body and that forms an elevator housing space; a proximal end wall portion that is provided at the distal-end-portion main body or the elevator-housing-space forming member and at which a lead-out port for a treatment tool opens; a first wall portion that extends from the proximal end wall portion to the distal end side of the distal-end-portion main body, the first wall portion being provided at a position on one direction side of a first direction perpendicular to the longitudinal axis of the distal-end-portion main body with respect to the lead-out port; a second wall portion that is provided at the elevator-housing-space forming member and that forms, together with the proximal end wall portion and the first wall portion, the elevator housing space, the second wall portion facing the first wall portion at a position on the other direction side opposite to the one direction side with respect to the lead-out port; a treatment tool elevator that is disposed in the elevator housing space and that is rotatable between a lying position and an elevated position about a rotary shaft parallel to the first direction, the treatment tool elevator having an elevator main body portion rotatably held by the rotary shaft, an elevator distal end portion provided on the distal end side of the elevator main body portion, and a wire connection portion provided at the elevator distal end portion; and an operating wire that is connected to the wire connection portion and that rotates the treatment tool elevator. When viewed in a second direction perpendicular to both the longitudinal axis and the first direction, a wire distal end portion of the operating wire connected to the wire connection portion is positioned on the other direction side with respect to the elevator main body portion. The second wall portion has a first wall surface at least a portion of which has a shape along the trajectory of the wire connection portion that rotates about the rotary shaft, and a second wall surface that is provided at a position on the one direction side with respect to the first wall surface and that has a shape extending along the trajectory of the elevator main body portion that rotates about the rotary shaft. The second wall surface overlaps at least a portion of the wire distal end portion in the first direction when viewed in the second direction.

In the treatment tool elevating mechanism according to another aspect of the present invention, the second wall surface is provided at a position on the one direction side with respect to the center axis of the wire distal end portion when viewed in the second direction.

The present invention is capable of achieving improvement in accessibility of a cleaning brush, prevention of wear of a distal-end-portion main body, and prevention of slipping of a treatment tool into the lower side of an operating wire.

DESCRIPTION OF THE PREFERRED EMBODIMENTS

Overall Configuration of Endoscope and Endoscope System

Figure 1:
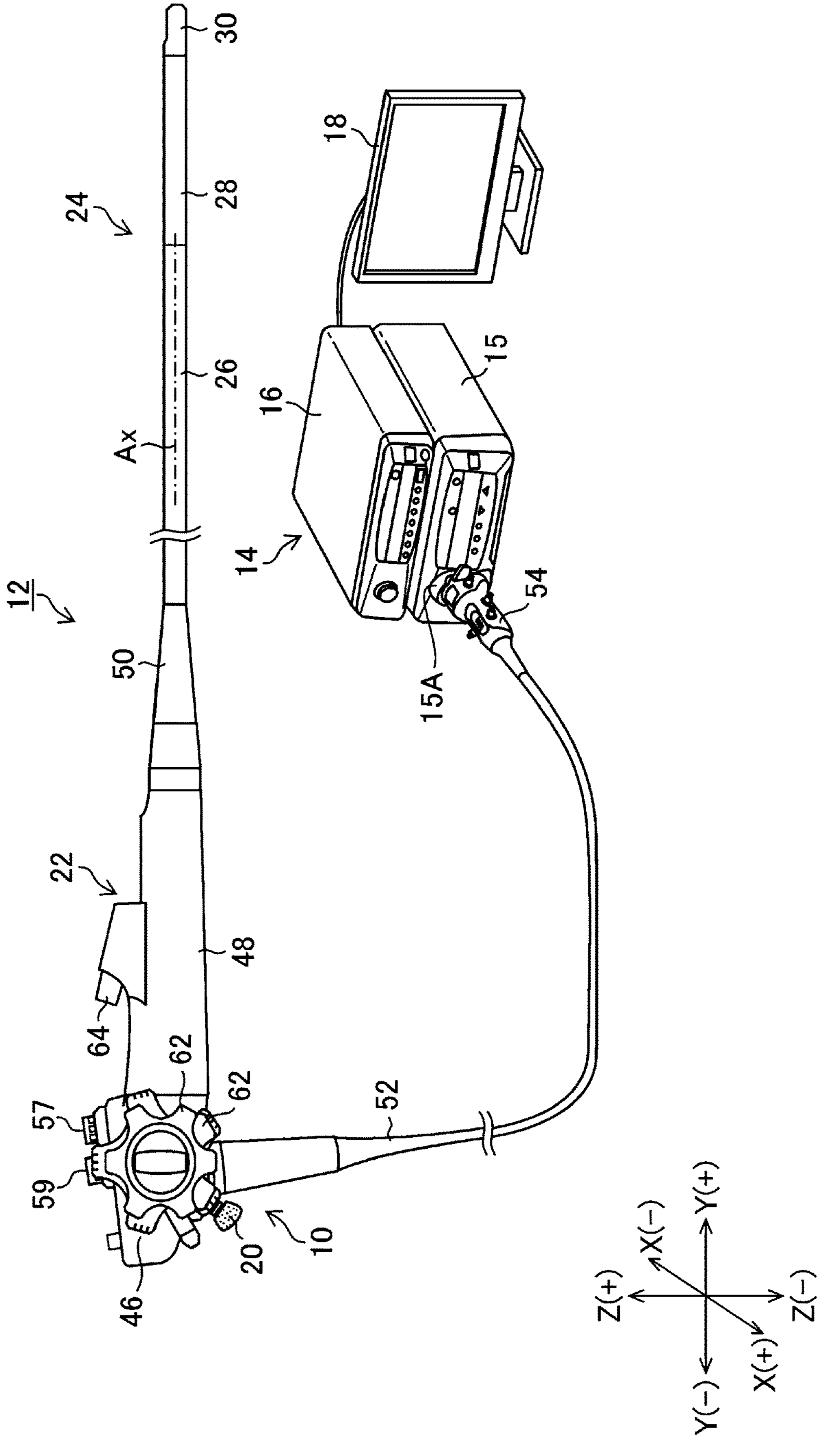
FIG. 1 is a configuration diagram of an endoscope system including an endoscope according to the present invention.

FIG. 1 is a configuration diagram of an endoscope system 12 including an endoscope 10 according to the present invention. The endoscope system 12 includes the endoscope 10, an endoscopic processor device 14, and a display 18.

The endoscope 10 is, for example, a side-viewing endoscope to be used as a duodenoscope. The endoscope 10 includes an operation section 22 provided with an elevation operation lever 20, and an insertion section 24 connected to the operation section 22 and to be inserted into a subject. The elevation operation lever 20 corresponds to the operating member in the present invention.

The insertion section 24 is inserted into a subject via the oral cavity and further inserted from the esophagus to the duodenum via the stomach. Consequently, a predetermined examination or treatment such as therapy of the duodenum is performed by using a treatment tool (not illustrated; the same applies to the followings) inserted into the insertion section 24. An example of the treatment tool is biopsy forceps having, at a tip portion thereof, a cup in which a biological tissue can be collected, an endoscopic sphincterotomy (EST) knife, a contrast tube, or the like.

The insertion section 24 has a long axis direction Ax (corresponding to the longitudinal axis in the present invention) extending from the proximal end side toward the distal end side thereof, and includes a soft portion 26, a bending portion 28, and an insertion-section distal end portion 30 in the order from the proximal end side toward the distal end side. The detailed configuration of the insertion-section distal end portion 30 will be described later. First, a schematic configuration of the insertion-section distal end portion 30 will be described.

Figure 2:
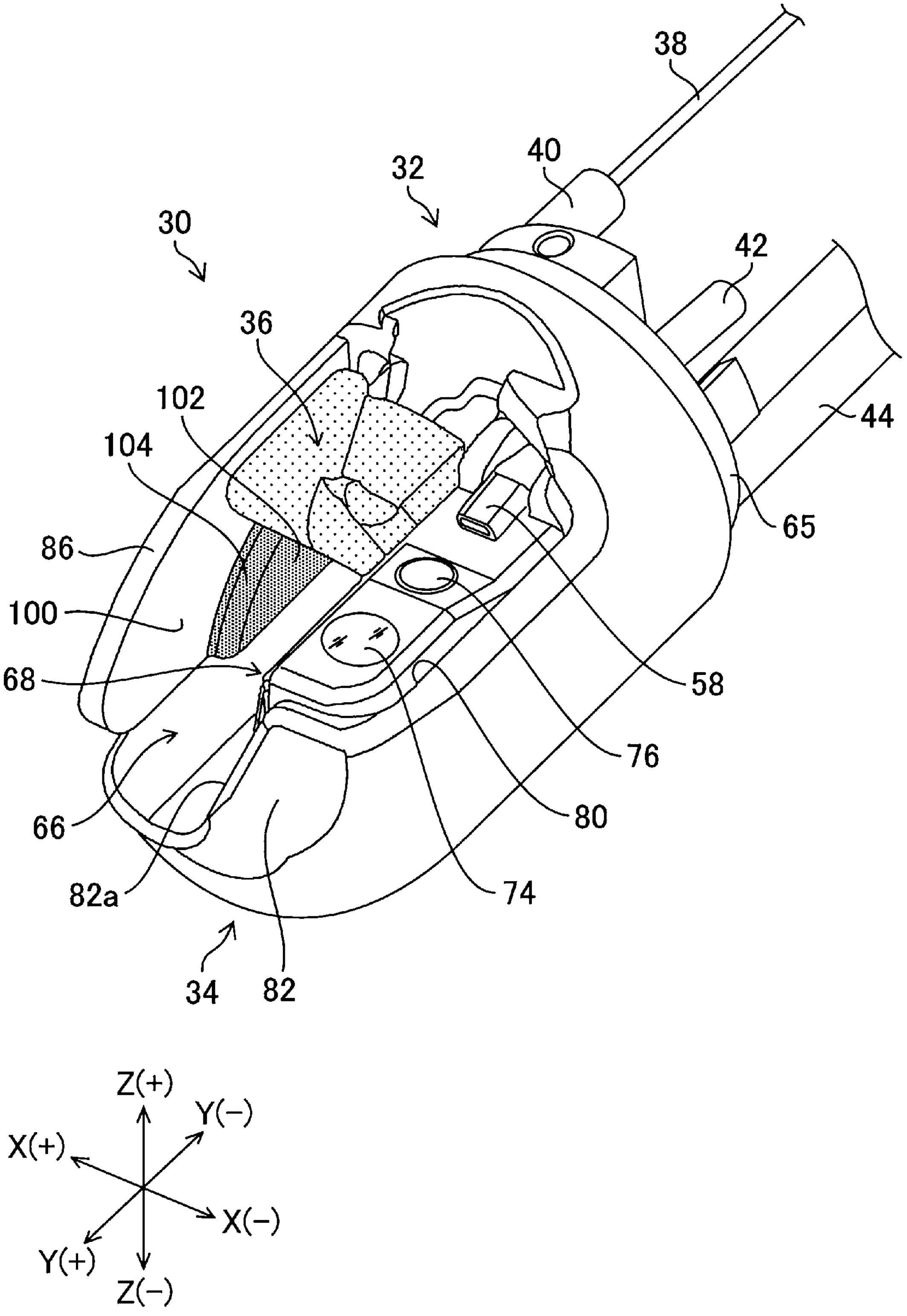
FIG. 2 is a perspective view of an insertion-section distal end portion.
Figure 3:
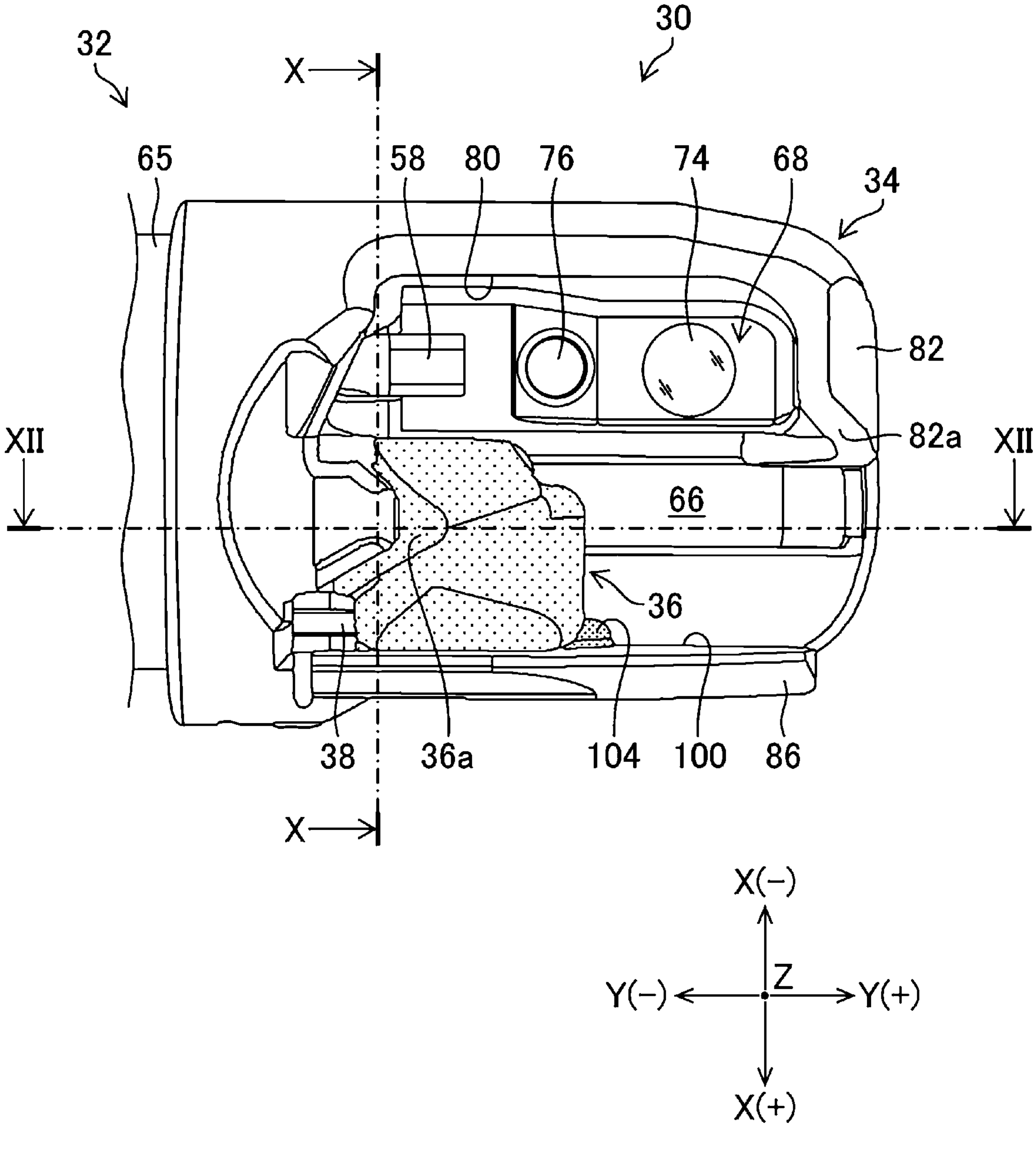
FIG. 3 is a top view of an insertion-section distal end portion.

FIG. 2 is a perspective view of the insertion-section distal end portion 30. FIG. 3 is a top view of the insertion-section distal end portion 30. As illustrated in FIG. 2 and FIG. 3, the insertion-section distal end portion 30 includes a distal-end-portion main body 32 and a cap 34 detachably attached to the distal-end-portion main body 32. At the insertion-section distal end portion 30, an elevator housing space 66 is formed by the distal-end-portion main body 32 and the cap 34. At the cap 34, a treatment tool elevator 36 having a treatment tool guide surface **36*a* is rotatably provided. The treatment tool elevator 36 is rotatable between a lying position and an elevated position inside the elevator housing space 66. In FIG. 2 and FIG. 3, a state in which the treatment tool elevator 36** is displaced to the elevated position is illustrated.

Various contents that are disposed in the inside of the insertion section 24 are connected to or inserted into the insertion-section distal end portion 30. Examples of the contents are a treatment tool channel 37 (refer to FIG. 12), an operating wire 38, a wire channel 40, an air/water supply tube 42, and a cable insertion channel 44.

The treatment tool channel 37 (refer to FIG. 12) leads a treatment tool tip portion (not illustrated; the same applies to the followings), which is a tip portion of a treatment tool, to a treatment tool lead-out port 60 (refer to FIG. 4) formed at the distal-end-portion main body 32. The operating wire 38 is formed integral with the treatment tool elevator 36, and the treatment tool elevator 36 is rotated to change the lead-out direction of the treatment tool tip portion that is led out from the distal-end-portion main body 32. The operating wire 38 is inserted into the wire channel 40. In FIG. 3 and subsequent figures, illustration of the wire channel 40 is omitted, as appropriate, to prevent complication of the drawings.

Air or water supplied from the operation section 22 is supplied through the air/water supply tube 42 to an air/water supply nozzle 58 of the distal-end-portion main body 32. A light guide that leads illumination light supplied from a light source device 15 (refer to FIG. 1), which will be described later, to an illumination window 74 of the distal-end-portion main body 32, a signal cable of an imaging portion (not illustrated) disposed inside an observation window 76, and the like are inserted into the cable insertion channel 44.

In the present description, a three-dimensional orthogonal coordinate system of mutually orthogonal three axial directions (X direction, Y direction, and Z direction) is used for description. That is, with the insertion-section distal end portion 30 viewed from the operation section 22, when a direction in which a treatment tool (not illustrated) is led out by the treatment tool elevator 36 is the upward direction, the upward direction is defined as the Z(+) direction, and the downward direction, which is a direction opposite to the upward direction, is defined as the Z(−) direction. In such a case, the rightward direction is defined as X(+) direction, and the leftward direction is defined as X(−) direction. In addition, in such as case, the forward direction (the distal end direction in the long axis direction Ax) is defined as Y(+) direction, and the rearward direction (the proximal end direction in the long axis direction Ax) is defined as Y(−) direction.

The X direction including the X(+) direction and the X(−) direction corresponds to the first direction in the present invention. The Y direction including the Y(+) direction and the Y(−) direction is parallel to the long axis direction Ax of the insertion section 24. The Z direction including the Z(+) direction and the Z(−) direction corresponds to the second direction perpendicular to both the longitudinal axis and the first direction in the present invention.

Referring back to FIG. 1, the soft portion 26 has a spiral tube (not illustrated) formed by winding a band-shaped thin elastic metal plate into a spiral shape; a tubular net body (not illustrated) knitted with metal wires and covering an outer portion of the spiral tube; and outer sheath (not illustrated) formed of a resin and covering the outer peripheral surface of the net body.

The bending portion 28 includes a structure body in which a plurality of angle rings (not illustrated) are rotatably connected to each other; a tubular metal-wire net body covering the outer periphery of the structure body; and a rubber outer sheath covering the outer peripheral surface of the net body. For example, four angle wires (not illustrated) are disposed from the bending portion 28 to a pair of later-described angle knobs 62 of the operation section 22.

The operation section 22 has a substantially cylindrical shape as a whole. The operation section 22 has an operation-section main body 46 and a grip portion 48 connected to the operation-section main body 46. On the distal end side of the grip portion 48, a proximal end portion (soft portion 26) of the insertion section 24 is provided via a bend stopper tube 50.

The grip portion 48 is to be gripped by an operator during operation of the endoscope 10. The grip portion 48 is provided with a treatment tool lead-in port 64 through which a treatment tool is led in. A treatment tool led in through the treatment tool lead-in port 64 is led out to the outside through the treatment tool lead-out port 60 (refer to FIG. 4) via the treatment tool channel 37 (refer to FIG. 12).

A proximal end portion of a universal cable 52 is connected to the operation-section main body 46. A distal end portion of the universal cable 52 is provided with a connector device 54. The connector device 54 is connected to the endoscopic processor device 14.

The endoscopic processor device 14 includes the light source device 15 and an image processing device 16. The light source device 15 includes a processor-side connector 15A to which the connector device 54 is connected. To the image processing device 16, the display 18 that displays an image that has been subjected to image processing in the image processing device 16 is connected.

The connector device 54 and the processor-side connector 15A transmit illumination light, electric power, imaging signals, and the like in a contactless manner (wired transmission is also possible) between the endoscope 10 and the endoscopic processor device 14. Consequently, the illumination light from the light source device 15 exits through the illumination window 74 (refer to FIG. 2) provided at the distal-end-portion main body 32 via the light guide (optical fiber cable; not illustrated). An imaging signal of an image imaged by the imaging portion (not illustrated) inside the observation window 76 is subjected to image processing by the image processing device 16 and is displayed as an image on the display 18.

The operation-section main body 46 is provided with an air/water supply button 57, a suction button 59, the pair of angle knobs 62, and the elevation operation lever 20.

The air/water supply button 57 is a button on which a two-stage pressing operation can be performed and is connected to the air/water supply tube 42 and an air/water supply source (not illustrated). A pressing operation of the air/water supply button 57 to the first stage causes air to be ejected from the air/water supply source through the air/water supply nozzle 58 via the air/water supply tube 42. A pressing operation of the air/water supply button 57 to the second stage causes water to be ejected from the air/water supply source through the air/water supply nozzle 58 via the air/water supply tube 42.

The suction button 59 is connected to the treatment tool channel 37 (refer to FIG. 12) and a negative pressure source (not illustrated). When the suction button 59 is pressed, air is sucked by the negative pressure source through the treatment tool lead-out port 60 (refer to FIG. 4) via the treatment tool channel 37. Consequently, it is possible to suck a body fluid such as blood through the treatment tool lead-out port 60.

The pair of angle knobs 62 are provided to be rotatable on the same axis at the operation-section main body 46. A proximal end portion on the opposite side of the distal end portion of each angle wire (not illustrated) connected to the bending portion 28 is connected to the pair of angle knobs 62. Each angle wire is operated to be pushed and pulled by the rotation operation of each of the pair of the angle knobs 62, and the bending portion 28 is thereby bent upward, downward, leftward, and rightward.

The elevation operation lever 20 is provided to be rotatable together with the pair of angle knobs 62 on the same axis at the operation-section main body 46 and is operated to rotate by the hand of an operator gripping the grip portion 48. A proximal end portion on the opposite side of a distal end portion of the operating wire 38 formed integral with the treatment tool elevator 36 is connected to the elevation operation lever 20 via a link mechanism (not illustrated). Consequently, a rotation operation of the elevation operation lever 20 pushes and pulls the operating wire 38 and thereby changes the orientation of the treatment tool elevator 36 between the lying position and the elevated position (refer to FIG. 12).

Configuration of Distal End Portion

Next, the detailed structure of the insertion-section distal end portion 30 will be described. As described above, the insertion-section distal end portion 30 includes: the distal-end-portion main body 32; the cap 34 detachably attached to the distal-end-portion main body 32; and the treatment tool elevator 36 formed integral with the operating wire 38.

Distal-End-Portion Main Body

Figure 4:
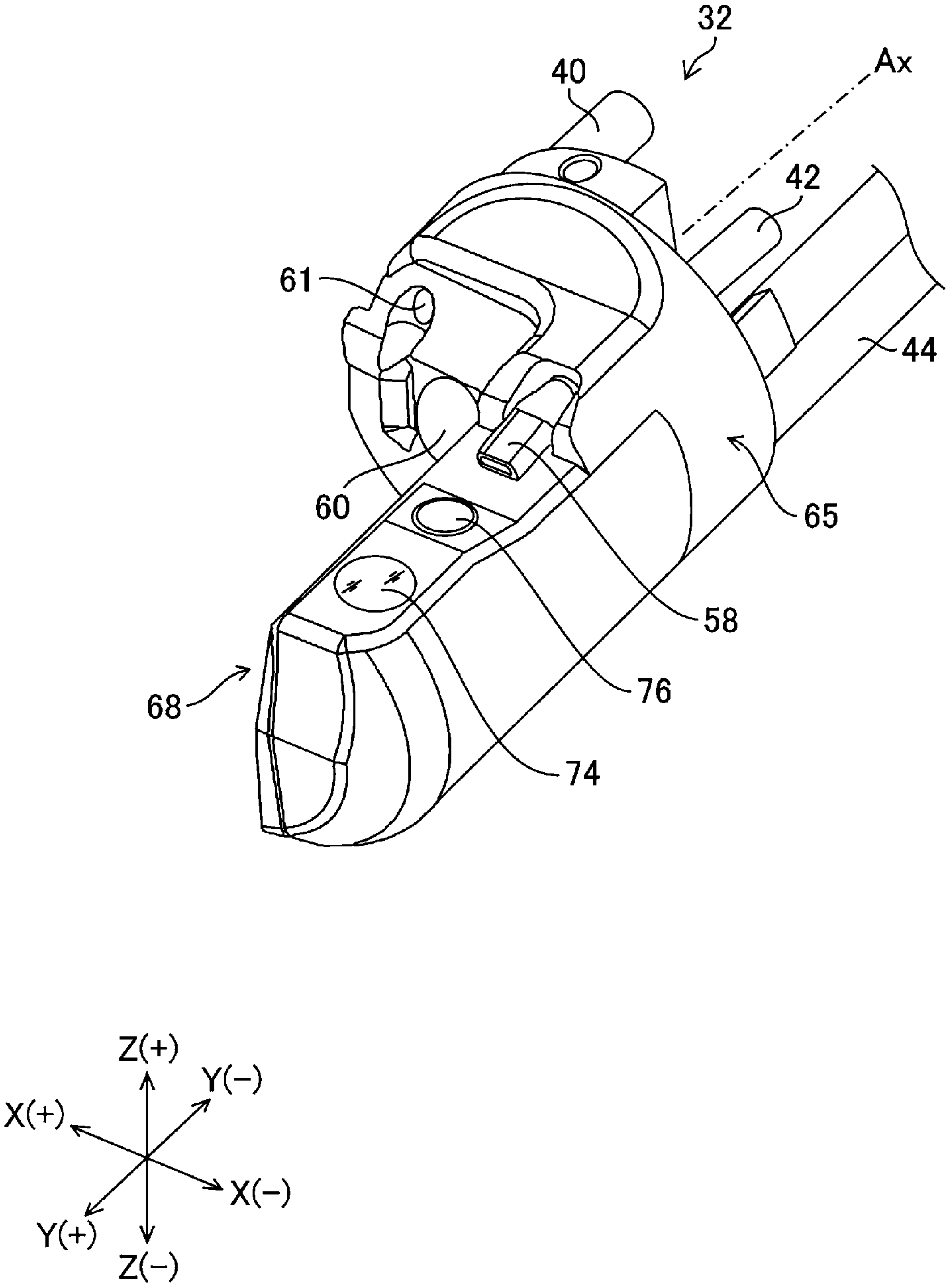
FIG. 4 is a perspective view of a distal-end-portion main body.

FIG. 4 is a perspective view of the distal-end-portion main body 32. As illustrated in FIG. 4 and aforementioned FIG. 2 and FIG. 3, the distal-end-portion main body 32 has a substantially L-shape when viewed from the Z(+) direction side and includes a proximal end wall portion 65 and a first wall portion 68.

The distal end surface side of the distal-end-portion main body 32 on the Y(+) direction side is provided with the first wall portion 68 and the air/water supply nozzle 58. The treatment tool channel 37 (refer to FIG. 12), the wire channel 40, the air/water supply tube 42, and the cable insertion channel 44, which are described above, are connected to the proximal end surface side of the distal-end-portion main body 32 on the Y(−) direction side. In addition, various types of through holes extending through the distal-end-portion main body 32 in the Y direction are formed in the distal-end-portion main body 32. The through holes are, for example, the treatment tool lead-out port 60 and a wire insertion hole 61.

The treatment tool lead-out port 60 opens at the proximal end wall portion 65. The treatment tool lead-out port 60 opens inside the elevator housing space 66, which will be described later, and the aforementioned treatment tool channel 37 is connected to the treatment tool lead-out port 60.

Consequently, a treatment tool is led out to the outside through the treatment tool lead-out port 60 via the elevator housing space 66 (treatment tool elevator 36).

The wire insertion hole 61 is formed at a position that is on the X(+) direction side with respect to the treatment tool lead-out port 60 and that is shifted to the Z(+) direction side, and the aforementioned operating wire 38 is inserted into the wire insertion hole 61.

On the distal end surface side of the proximal end wall portion 65, the first wall portion 68 is provided at a position on the X(−) direction side perpendicular to the longitudinal axis (long axis direction Ax, Y direction) of the distal-end-portion main body 32 with respect to the treatment tool lead-out port 60. The first wall portion 68 has a shape extending on the Y(+) direction side, which is the distal end side of the distal-end-portion main body 32. In this case, the X(−) direction side is a direction perpendicular to the longitudinal axis (long axis direction Ax) of the distal-end-portion main body 32 and corresponds to the one direction side in the first direction in the present invention.

The first wall portion 68 forms, between the first wall portion 68 and the later-described cap 34, the elevator housing space 66 that houses (capable of completely housing and partially housing) the treatment tool elevator 36. At the upper surface of the first wall portion 68 on the Z(+) direction side, the illumination window 74 and the observation window 76 are disposed adjacent to each other in the Y direction.

On the inner side of the illumination window 74, the exit end of the aforementioned light guide is disposed. Consequently, it is possible to illuminate the side where the elevator housing space 66 opens, that is, the Z(+) direction side of the elevator housing space 66 through the illumination window 74.

The imaging portion (not illustrated) is provided on the inner side of the observation window 76. The imaging portion images a photographic subject present on the Z(+) direction side of the elevator housing space 66 through the observation window 76. The imaging portion includes, for example, an imaging optical system (not illustrated) and an imaging element (not illustrated) of a complementary metal oxide semiconductor (CMOS) type or a charge coupled device (CCD) type. An imaging signal of the photographic subject output from the imaging element is input to the image processing device 16 via the signal cable (not illustrated), the connector device 54, and the processor-side connector 15A. Consequently, an image of the photographic subject is displayed on the display 18.

The air/water supply nozzle 58 is provided at a position on the distal end surface side of the distal-end-portion main body 32 and on the Z(+) direction side of the first wall portion 68, and air and water are jetted through the air/water supply nozzle 58 toward the observation window 76.

Cap

Figure 5:
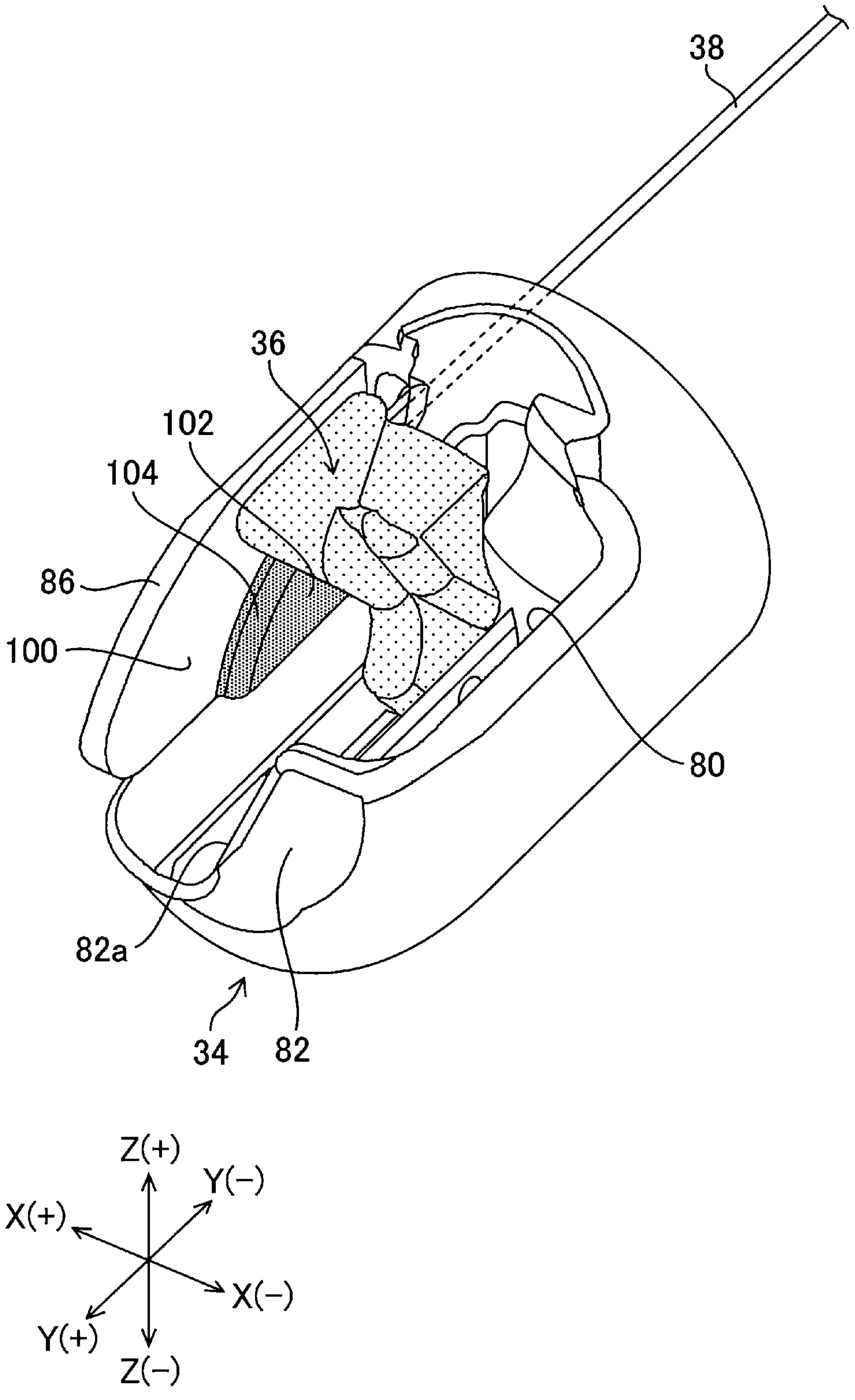
FIG. 5 is a perspective view of a cap to which a treatment tool elevator and an operating wire are attached.
Figure 6:
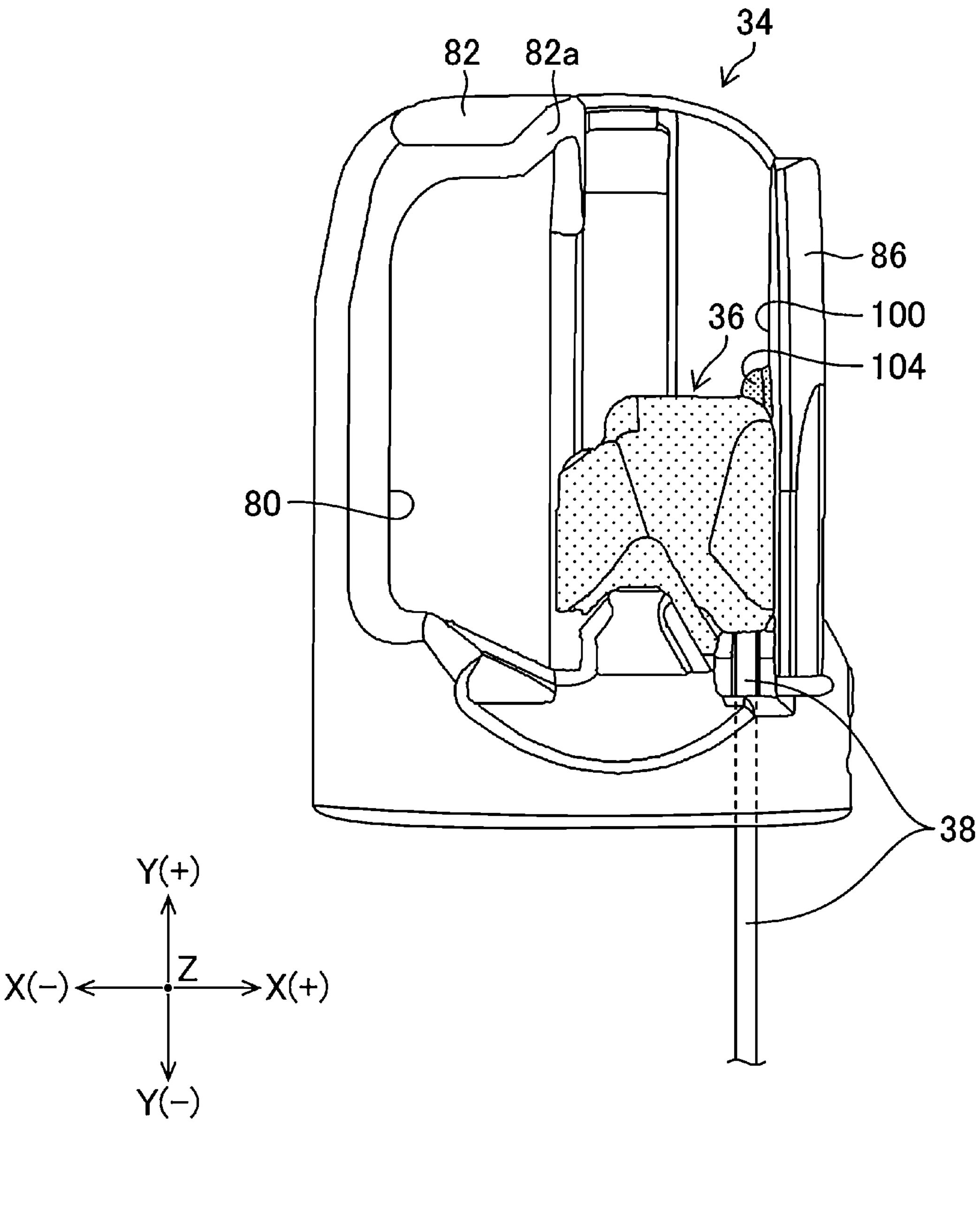
FIG. 6 is a top view of a cap to which a treatment tool elevator and an operating wire are attached.
Figure 7:
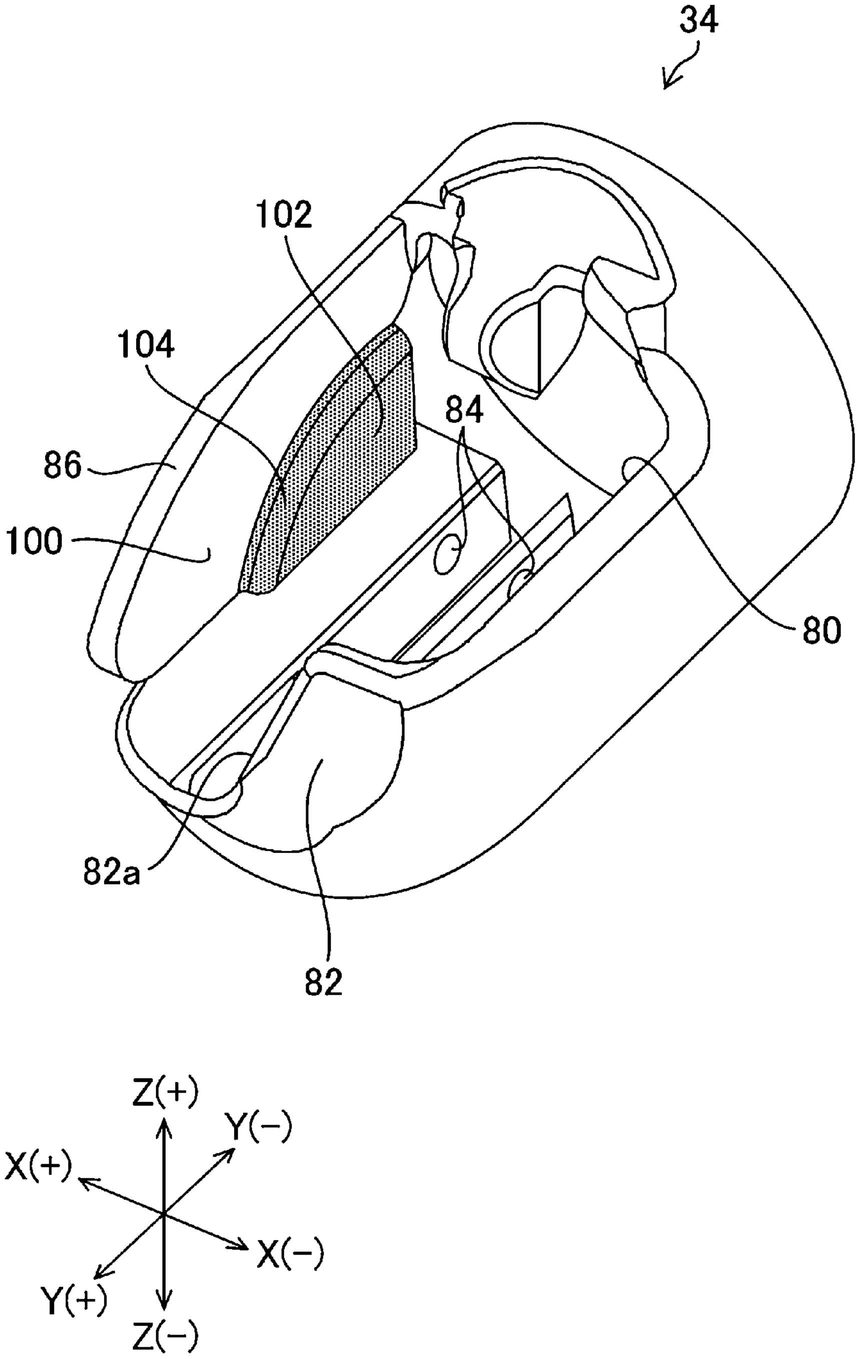
FIG. 7 is a perspective view of a cap from which a treatment tool elevator and an operating wire are detached.

FIG. 5 is a perspective view of the cap 34 to which the treatment tool elevator 36 and the operating wire 38 are attached. FIG. 6 is a top view of the cap 34 to which the treatment tool elevator 36 and the operating wire 38 are attached. FIG. 7 is a perspective view of the cap 34 from which the treatment tool elevator 36 and the operating wire 38 are detached.

As illustrated in FIG. 5 to FIG. 7 and aforementioned FIG. 2 and FIG. 3, the cap 34, the treatment tool elevator 36, and the operating wire 38 are disposable items (replaceable items) that are to be attached to the distal-end-portion main body 32 before the endoscope 10 is used (that is, before treatment, examination, and the like), and that are to be detached from the distal-end-portion main body 32 and discarded after the use is completed. The cap 34, the treatment tool elevator 36, and the operating wire 38 constitute the treatment tool elevating mechanism in the present invention.

The cap 34 has a substantially cylindrical shape with a bottom and is to be detachably attached to the distal-end-portion main body 32. The cap 34 corresponds to the elevator-housing-space forming member in the present invention. When attached to the distal-end-portion main body 32, the cap 34 forms, together with the proximal end wall portion 65 and the first wall portion 68, the elevator housing space 66 (refer to FIG. 2 and FIG. 3) that houses the treatment tool elevator 36. A first opening window 80, a cap distal end portion 82, an elevator holding portion 84, and a second wall portion 86 are formed at the cap 34.

When the insertion-section distal end portion 30 is viewed from a position on the Z(+) direction side of the insertion-section distal end portion 30, the first opening window 80 exposes the elevator housing space 66 and the upper surface (the illumination window 74, the observation window 76, and the like) of the first wall portion 68. Consequently, it is possible to lead out a treatment tool to the Z(+) direction side from the elevator housing space 66 and possible to illuminate and image the aforementioned photographic subject.

The cap distal end portion 82 covers the distal end surface on the Y(+) direction side of the distal-end-portion main body 32. A second opening window 82*a* (corresponding to the opening window in the present invention; refer to FIG. 13) that exposes the elevator housing space 66 when viewed from the distal end side of the cap 34 (when the cap 34 is viewed from a position on the Y(+) direction side of the cap 34) is formed at the cap distal end portion 82. The second opening window 82*a* has a shape suitable for insertion of fingers or a tool at the time of attaching and detaching of the cap 34 with respect to the distal-end-portion main body 32, in particular, at the time of detaching thereof. Consequently, it is possible to attach and detach the cap 34 easily.

The elevator holding portion 84 (refer to FIG. 7) is formed at a bottom portion of the inner peripheral surface of the cap 34 defining the bottom surface of the elevator housing space 66. The elevator holding portion 84 holds, via a rotary shaft 88 (refer to FIG. 12), the treatment tool elevator 36 so as to be rotatable between the lying position and the elevated position.

The second wall portion 86 is disposed at a position that is on the X(+) direction side with respect to the treatment tool lead-out port 60 and that faces the first wall portion 68 in a state in which the cap 34 is attached to the distal-end-portion main body 32. The second wall portion 86 has a shape extending on the Y(+) direction side, similarly to the first wall portion 68. In this case, the X(+) direction side corresponds to the other direction side in the first direction in the present invention. The second wall portion 86 and the first wall portion 68 define the width of the elevator housing space 66 in the X direction. A first wall surface 100, a second wall surface 102, and a step surface 104, which will be described later in detail, are formed, at the second wall portion 86, on the side facing the first wall portion 68 and the treatment tool elevator 36.

Treatment Tool Elevator and Operating Wire

Figure 8:
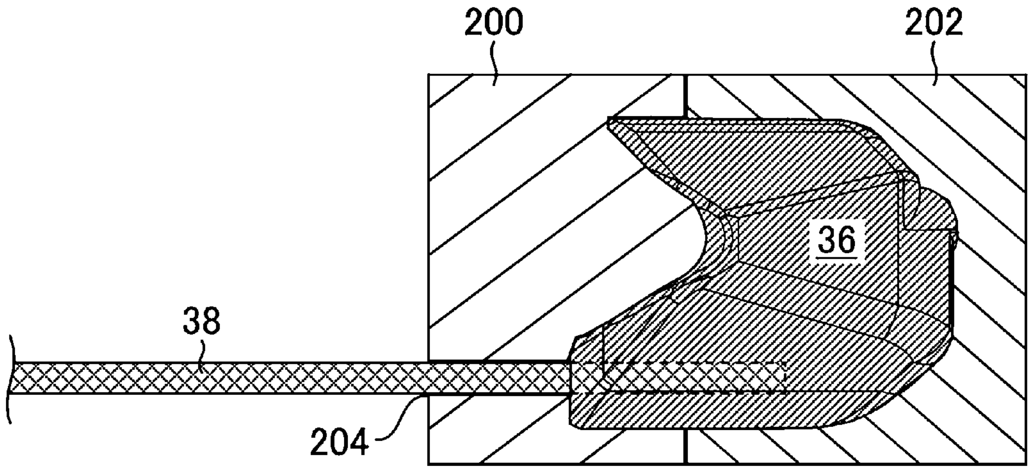
FIG. 8 is an explanatory view for describing a method of forming a treatment tool elevator and an operating wire.

FIG. 8 is an explanatory view for describing a method of forming the treatment tool elevator 36 and the operating wire 38. As illustrated in FIG. 8, the treatment tool elevator 36 and the operating wire 38 are an insert molded body integrated by a publicly known insert-molding method.

Specifically, a pair of a first metal mold 200 and a second metal mold 202 that form, in a state of being stacked together, a cavity (mold) corresponding to the treatment tool elevator 36 are prepared, and the first metal mold 200 and the second metal mold 202 are stacked together. Next, a distal end portion of the operating wire 38 is disposed in the inside of the cavity through a through hole 204 provided in the first metal mold 200. A material of the treatment tool elevator 36 is injected to fill the inside of the cavity and then cooled, thereby forming the insert molded body of the treatment tool elevator 36 and the operating wire 38. The method of insert-molding the treatment tool elevator 36 and the operating wire 38 is not limited to the method described above. As the method, publicly known various insert-molding methods may be employed.

Figure 9:
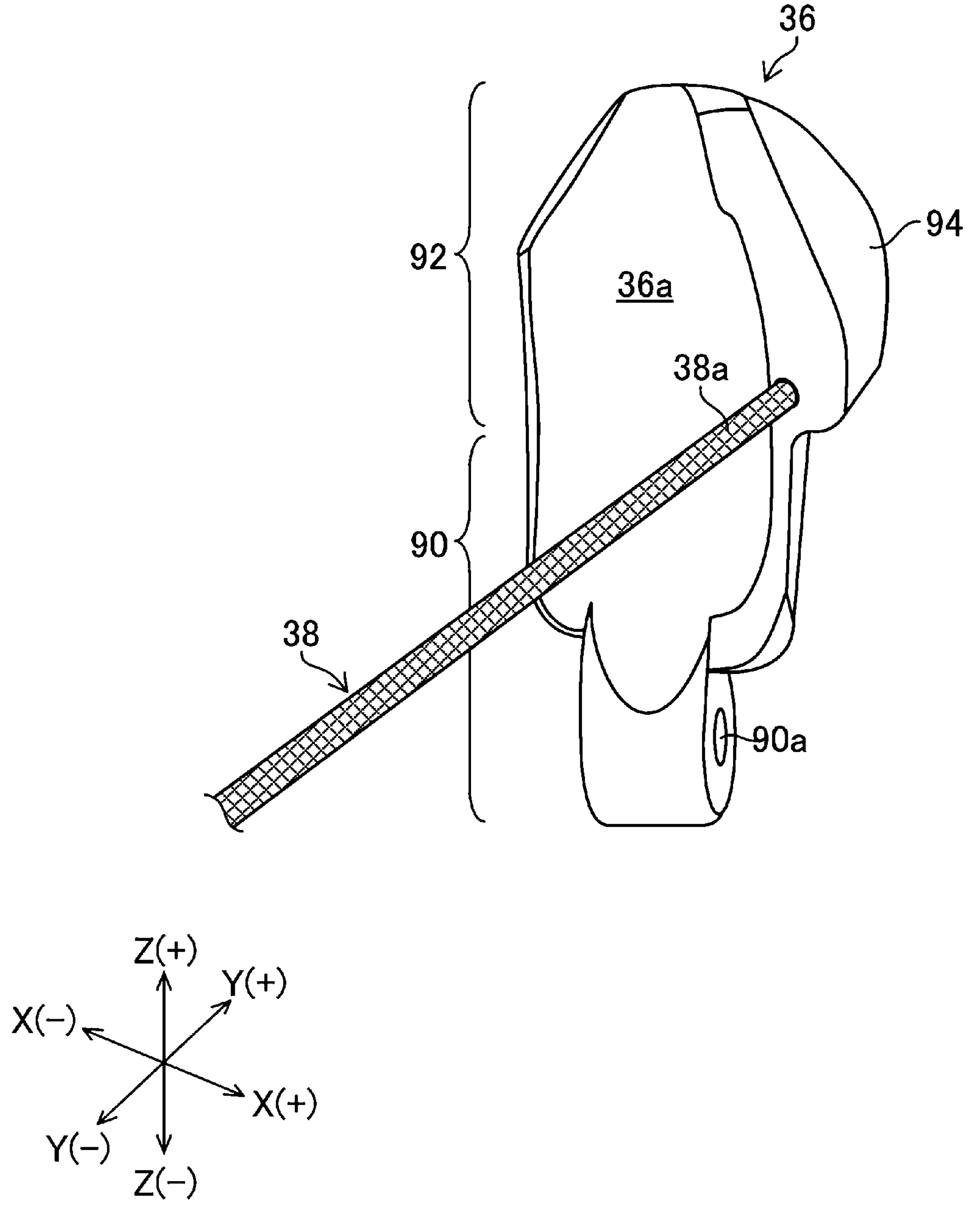
FIG. 9 is a perspective view of a treatment tool elevator and an operating wire.

FIG. 9 is a perspective view of the treatment tool elevator 36 and the operating wire 38. As illustrated in FIG. 9 and aforementioned FIG. 2 to FIG. 6, the treatment tool guide surface 36*a* that faces the treatment tool lead-out port 60 when the treatment tool elevator 36 is attached together with the cap 34 to the distal-end-portion main body 32 is formed at the treatment tool elevator 36. The treatment tool guide surface 36*a* changes the advancing direction of the treatment tool tip portion led out to the inside of the elevator housing space 66 through the treatment tool lead-out port 60, to a direction toward the first opening window 80 (the outside of the elevator housing space 66).

The treatment tool elevator 36 includes an elevator main body portion 90, an elevator distal end portion 92, and a wire connection portion 94. The elevator main body portion 90 has, at a proximal end portion thereof, an insertion hole 90*a* into which the rotary shaft 88 (refer to FIG. 12) is inserted. The elevator main body portion 90 is rotatably held by the elevator holding portion 84 via the rotary shaft 88. The elevator distal end portion 92 is provided on the distal end side (on the opposite direction side of the direction toward the insertion hole 90*a* and the rotary shaft 88) of the elevator main body portion 90.

The wire connection portion 94 is provided at a side surface on the X(+) direction side of the elevator distal end portion 92 and has a shape projecting from the side surface on the X(+) direction side and projecting further on the X(+) direction than at least the elevator main body portion 90. A wire distal end portion 38*a*, which is a distal end portion of the operating wire 38, is connected to (held by) the wire connection portion 94.

The wire distal end portion 38*a* is connected to the wire connection portion 94 and is exposed in the inside of the elevator housing space 66 in accordance with the orientation of the treatment tool elevator 36. The wire distal end portion 38*a* is positioned on the X(+) direction side with respect to the elevator main body portion 90 when the insertion-section distal end portion 30 is viewed from a position on the Z(+) direction side (corresponding to the second direction) of the insertion-section distal end portion 30.

In a case where the position of the wire distal end portion 38*a* (wire connection portion 94) is on the X(+) direction side with respect to the elevator main body portion 90, as described above, if a gap is formed at a position on the Z(−) direction side of the wire distal end portion 38*a*, there is a likelihood of the treatment tool tip portion slipping into the inside of the gap. Thus, in the present embodiment, a structure (the first wall surface 100, the second wall surface 102, and the step surface 104) that fills the above-described gap is formed at the second wall portion 86 of the cap 34.

First Wall Surface, Second Wall Surface, and Step Surface

Figure 10:
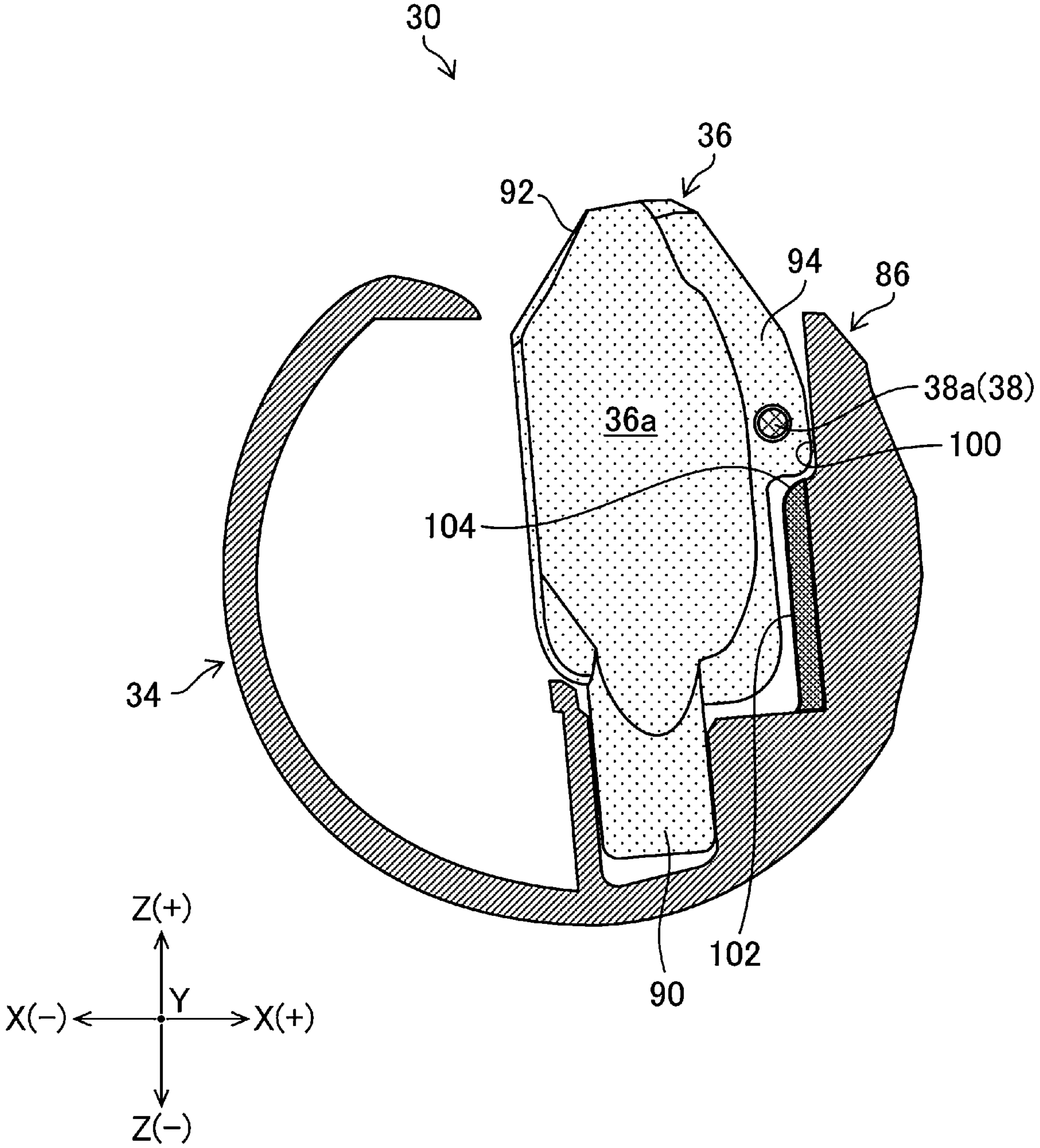
FIG. 10 is a sectional view of an insertion-section distal end portion along line X-X in FIG. 3.
Figure 11:
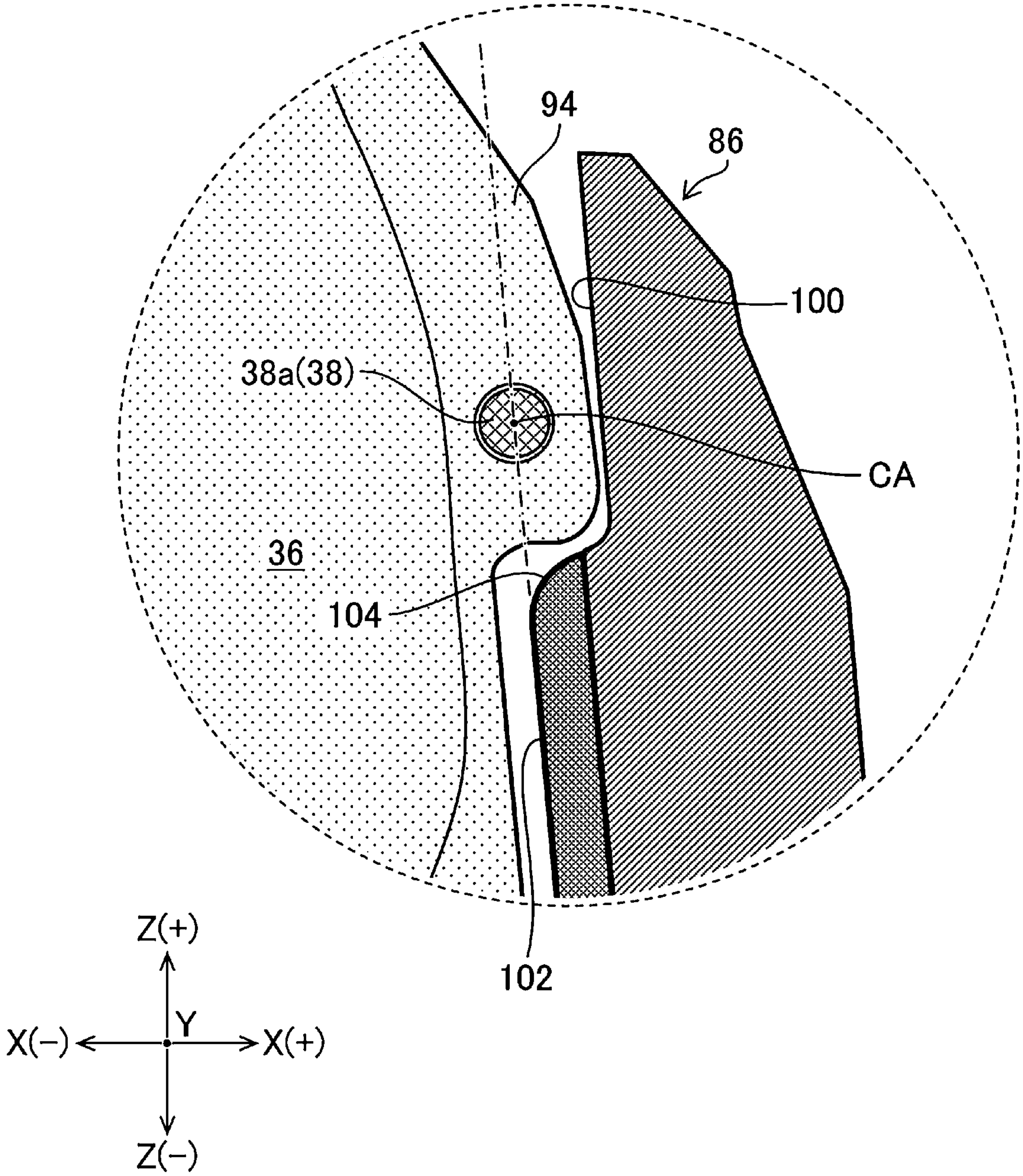
FIG. 11 is an enlarged view of a partial region in FIG. 10.
Figure 12:
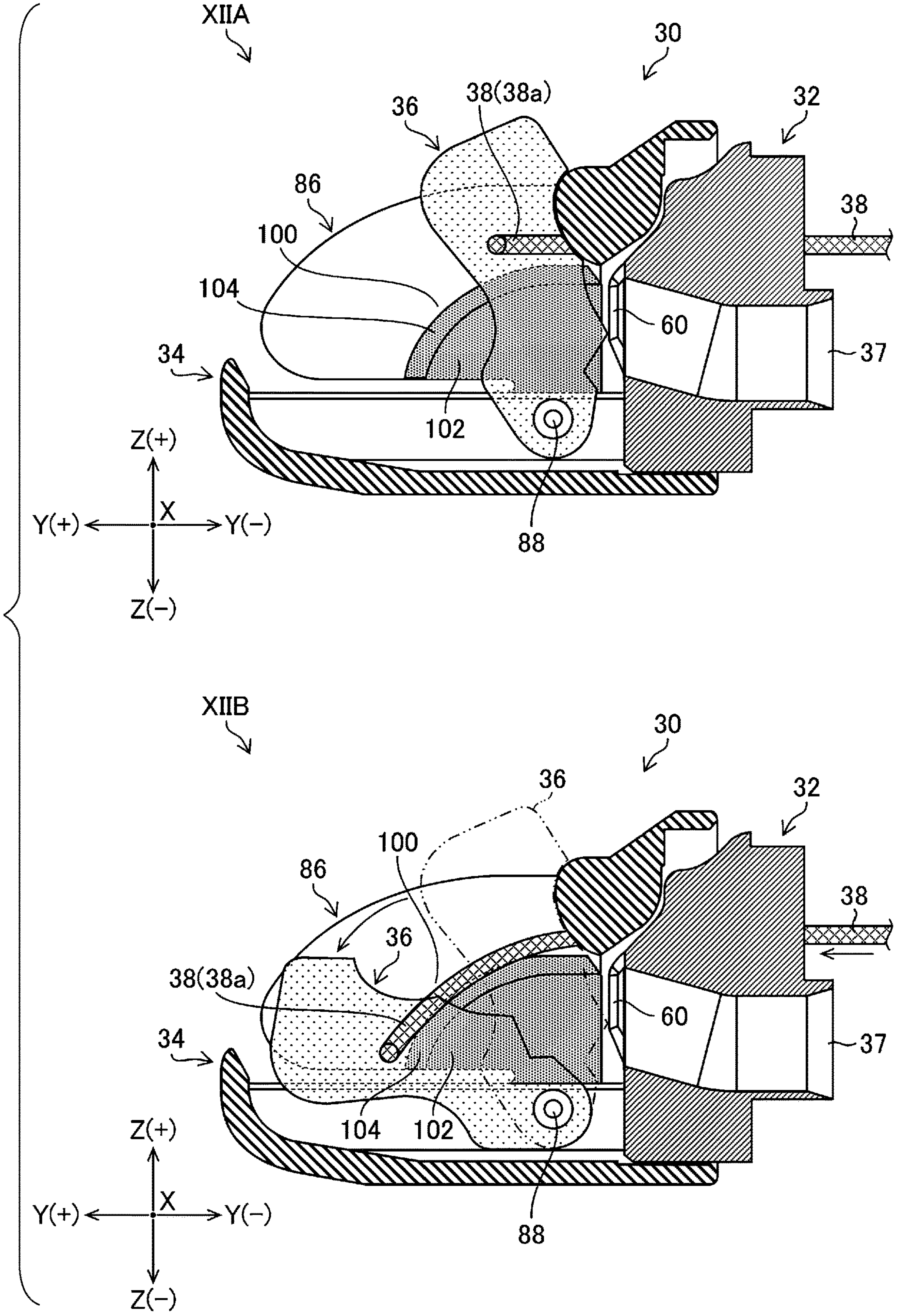
FIG. 12 is a sectional view of an insertion-section distal end portion along line XII-XII in FIG. 3.
Figure 13:
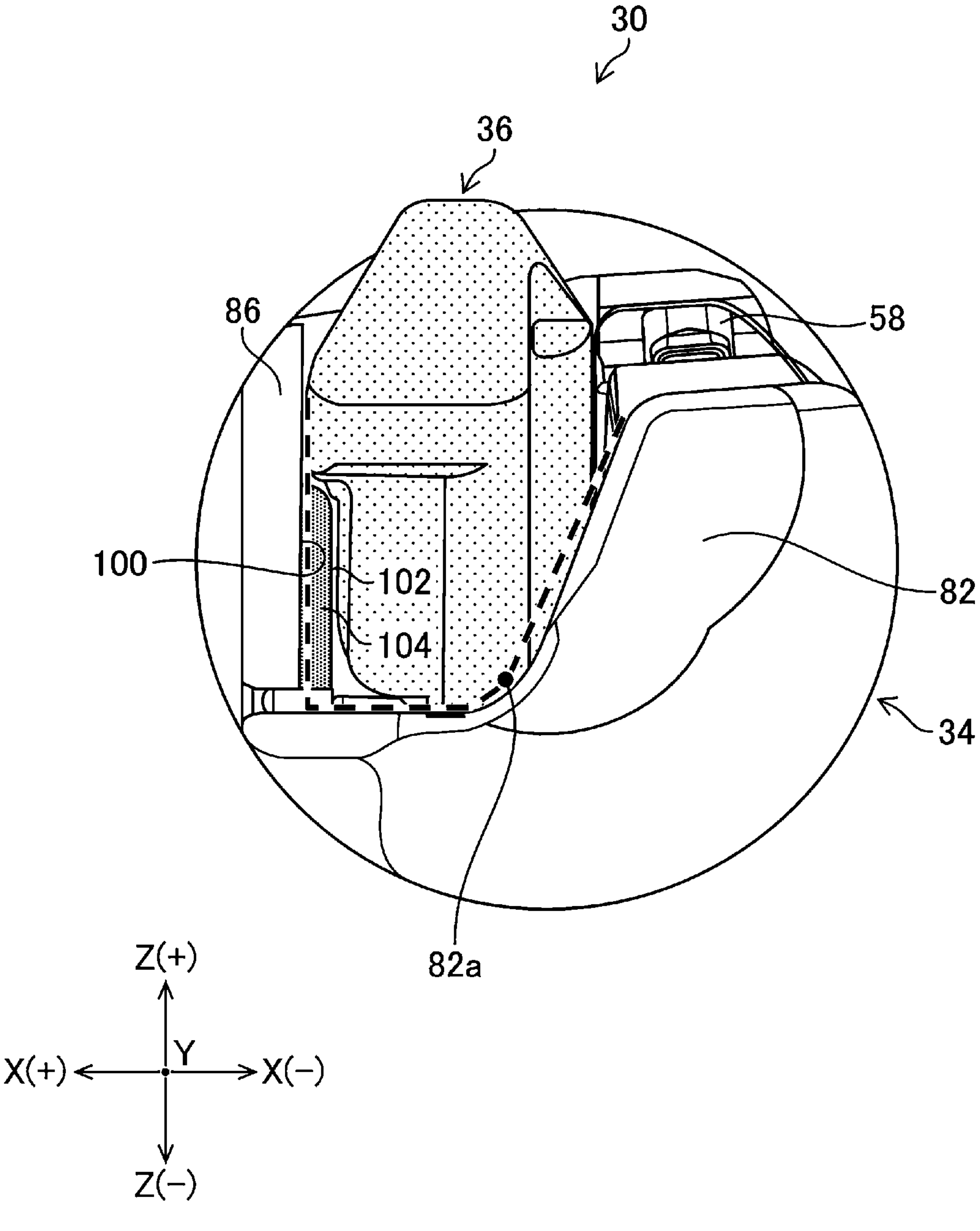
FIG. 13 is a front view of an insertion-section distal end portion viewed from a position on the Y(+) direction side of a distal end portion.

FIG. 10 is a sectional view of the insertion-section distal end portion 30 along line X-X in FIG. 3. FIG. 11 is an enlarged view of a partial region in FIG. 10. FIG. 12 is a sectional view of the insertion-section distal end portion 30 along line XII-XII in FIG. 3. FIG. 13 is a front view of the insertion-section distal end portion 30 viewed from a position on the Y(+) direction side of the insertion-section distal end portion 30.

As illustrated in FIG. 10 to FIG. 13, in the second wall portion 86, the first wall surface 100 is formed at a position that faces the wire connection portion 94 (wire distal end portion 38*a*) of the treatment tool elevator 36 that rotates about the rotary shaft 88. In other words, the first wall surface 100 is formed at a position on the X(+) direction side with respect to the wire connection portion 94 and the wire distal end portion 38*a* when the insertion-section distal end portion 30 is viewed from a position on the Z(+) direction side of the insertion-section distal end portion 30. As the distance from the first wall surface 100 to the wire connection portion 94 and the wire distal end portion 38*a* in the X direction is increased, the width (thickness) of the elevator distal end portion 92 including the wire connection portion 94 in the X direction can be increased. Therefore, it is possible to increase the fluidity of the material at the time of insert-molding of the treatment tool elevator 36 and the like illustrated in aforementioned FIG. 8.

When the second wall portion 86 is viewed from a position on the X(−) direction side of the second wall portion 86, the first wall surface 100 has a shape in which at least a portion extends along the trajectory of the wire connection portion 94 that rotates about the rotary shaft 88. The first wall surface 100 of the present embodiment includes a region having a shape extending along the aforementioned trajectory, and an extending region that extends from the region on the distal end side (Y(+) direction side) of the insertion-section distal end portion 30. The shape of the first wall surface 100 is, however, not particularly limited as long as the first wall surface 100 includes at least the former region.

In the second wall portion 86, the second wall surface 102 is formed at a position facing the elevator main body portion 90 of the treatment tool elevator 36 that rotates about the rotary shaft 88, the position being on the X(−) direction side with respect to the first wall surface 100. Specifically, when the second wall portion 86 is viewed from a position on the X(−) direction side of the second wall portion 86, the second wall surface 102 has a shape extending along the trajectory of the elevator main body portion 90 that rotates about the rotary shaft 88.

When the insertion-section distal end portion 30 is viewed from a position on the Z(+) direction side (corresponding to the second direction) of the insertion-section distal end portion 30, the second wall surface 102 overlaps at least a portion of the wire distal end portion 38*a* (wire connection portion 94) in the X direction. Therefore, the second wall surface 102 is formed at a position where the gap on the Z(−) direction side of the wire distal end portion 38*a* is filled. Consequently, it is possible to prevent the treatment tool tip portion from slipping into the gap.

At this time, from a point of view of reliably preventing the treatment tool tip portion from slipping into a position on the Z(−) direction side of the wire distal end portion 38*a*, the second wall surface 102 is preferably formed at a position (including the position of a center axis CA) on the X(−) direction side with respect to the center axis CA (refer to FIG. 11) of the wire distal end portion 38*a* when the insertion-section distal end portion 30 is viewed from a position on the Z(+) direction side of the insertion-section distal end portion 30. In this case, the position of the second wall surface 102 is adjusted to an appropriate position between the center axis CA and the elevator main body portion 90 in the X direction to prevent the second wall surface 102 from interfering with the treatment tool tip portion that has a large diameter. The step amount (height difference) between the first wall surface 100 and the second wall surface 102 in the X direction is, for example, 1 mm to 2 mm.

The step surface 104 is a connection surface (boundary surface) that is formed between the first wall surface 100 and the second wall surface 102 and that connects the first wall surface 100 and the second wall surface 102 to each other. When the second wall portion 86 is viewed from a position on the X(−) direction side of the second wall portion 86, the step surface 104 has an arc shape extending along the trajectory of the wire distal end portion 38*a* that rotates integrally with the wire connection portion 94 about the rotary shaft 88. Consequently, the wire distal end portion 38*a* moves along the step surface 104 when the treatment tool elevator 36 is displaced between the elevated position (refer to the sign XIIA in FIG. 12) and the lying position (refer to the sign XIIB in FIG. 12). Accordingly, the step surface 104 also functions as a guide surface of the wire distal end portion 38*a*. The wire distal end portion 38*a* may be in sliding-contact with the step surface 104, or a gap may be present between the wire distal end portion 38*a* and the step surface 104 to an extent that can prevent the treatment tool tip portion from slipping into the gap.

Figure 14:
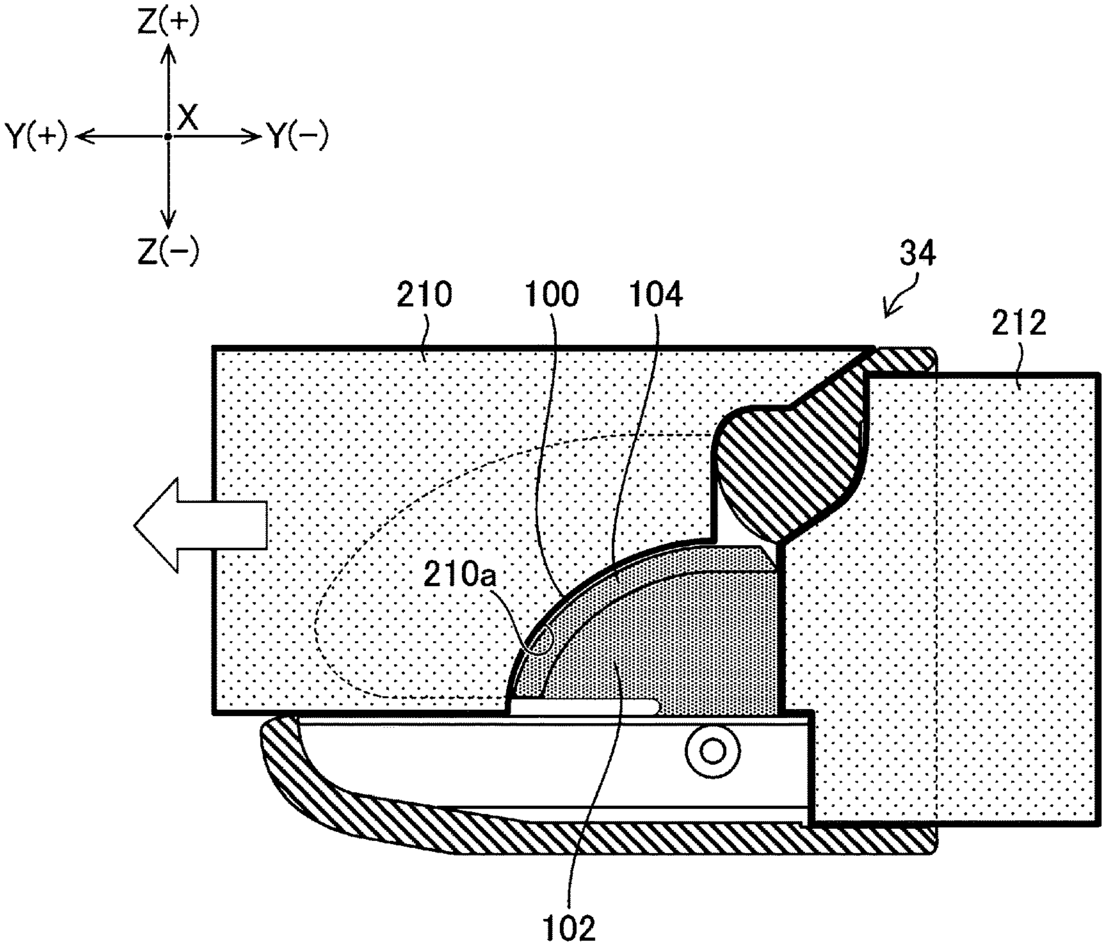
FIG. 14 is an explanatory view for describing formation of a cap, in particular, formation of a step surface of a second wall portion.

FIG. 14 is an explanatory view for describing formation of the cap 34, in particular, formation of the step surface 104 of the second wall portion 86. Regarding a first metal mold 210 and a second metal mold 212 in FIG. 14, illustration of portions not related to the formation of the step surface 104 is omitted, as appropriate, to prevent complication of the drawing.

As illustrated in FIG. 14, the cap 34 is formed by using a pair of the first metal mold 210 and the second metal mold 212. The first metal mold 210 and the second metal mold 212 are separable from each other and form, in a state of being stacked together, a cavity (mold) corresponding to the cap 34. A material of the cap 34 is injected into the cavity, cooled, and solidified. Thereafter, the first metal mold 210 and the second metal mold 212 are separated from each other to thereby form the cap 34.

Here, to form the arc-shaped step surface 104, it is necessary to separate the first metal mold 210 and the second metal mold 212 from each other toward the Y direction side or the Z direction side after solidification of the cap 34. However, considering the shapes of the other parts of the cap 34, it is difficult to separate the first metal mold 210 and the second metal mold 212 toward the Z direction side.

Thus, in the present embodiment, the first metal mold 210 and the second metal mold 212, such as those illustrated in FIG. 14, that are separable from each other toward the Y direction side are used. In the present embodiment, the second opening window 82*a* (refer to FIG. 13) that exposes the elevator housing space 66 is formed at the cap distal end portion 82. Therefore, it is possible to separate a mold surface 210*a* corresponding to the step surface 104 in the first metal mold 210 from the step surface 104 through the second opening window 82*a* toward the Y(+) direction side after solidification of the material of the cap 34.

As described above, it is possible in the present embodiment to prevent the treatment tool tip portion from slipping into a position on the Z(−) direction side of the wire distal end portion 38*a* by filling the gap generated on the Z(−) direction side of the wire distal end portion 38*a* with the second wall surface 102 and the step surface 104 formed at the second wall portion 86 of the cap 34. In addition, since providing the second wall portion 86 (the second wall surface 102 and the step surface 104) at the disposable-type cap 34 eliminates the need to provide a configuration corresponding to the second wall portion 86 at the distal-end-portion main body 32, accessibility of a cleaning brush with respect to the distal-end-portion main body 32 after the cap 34 is detached is prevented from being degraded. Further, even when the step surface 104 is worn by sliding with the wire distal end portion 38*a*, there is no problem since the cap 34 itself is discarded every time when the use of the endoscope 10 is completed. As a result, it is possible to achieve improvement in accessibility of a cleaning brush, prevention of wear of the distal-end-portion main body 32, and prevention of a treatment tool from slipping into the Z(−) direction side of the operating wire 38.

Treatment Tool Elevator in Another Embodiment

Figure 15:
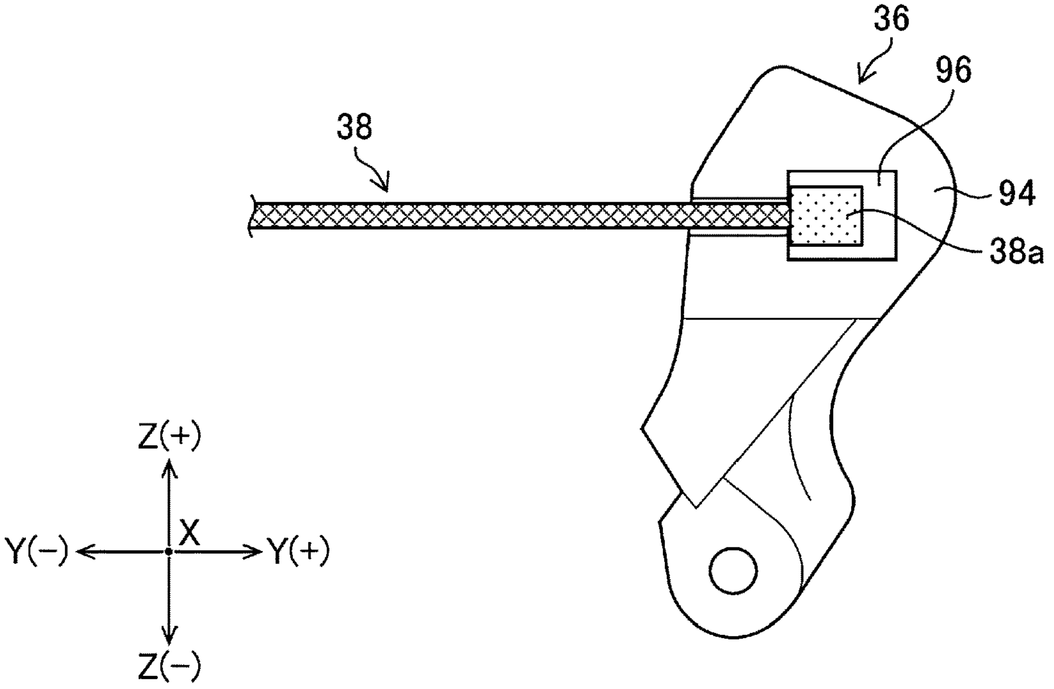
FIG. 15 is a side view of a treatment tool elevator according to another embodiment.

FIG. 15 is a side view of the treatment tool elevator 36 in another embodiment. While the treatment tool elevator 36 and the operating wire 38 are integrated with each other by insert-molding in the aforementioned embodiment, the treatment tool elevator 36 and the operating wire 38 may be formed as separate bodies as illustrated in FIG. 15. In this case, a wire attaching portion 96 to which the wire distal end portion 38*a* can be attached is formed at the wire connection portion 94 of the treatment tool elevator 36. An example of the wire attaching portion 96 is an engagement groove or the like with which the wire distal end portion 38*a* is to be engaged. The shape and the configuration of the wire attaching portion 96 are, however, not particularly limited as long as the wire distal end portion 38*a* can be attached to the wire attaching portion 96.

Also in such a treatment tool elevator 36 in the other embodiment, as the distance from the first wall surface 100 to the wire connection portion 94 and the wire distal end portion 38*a* in the X direction is increased, the width (thickness) of the elevator distal end portion 92 including the wire connection portion 94 in the X direction can be increased. It is thus possible to ensure stiffness of the treatment tool elevator 36.

Others

In the aforementioned embodiment, a method of forming the treatment tool elevator 36 and the operating wire 38 and a method of forming the cap 34 by using various metal molds have been described. These formation methods are, however, not particularly limited, and publicly known various methods can be employed.

In the aforementioned embodiment, the second opening window 82*a* is formed at the cap distal end portion 82. However, the second opening window 82*a* may be not necessarily formed at the cap distal end portion 82 in a case where the cap 34 can be formed using a metal mold of a vertical separation type or where the cap 34 is to be formed by a method other than metal molds (for example, by a 3D printer or the like).

In the aforementioned embodiment, a case where the cap 34, the treatment tool elevator 36, and the operating wire 38 are disposable items has been described. The cap 34, the treatment tool elevator 36, and the operating wire 38, however, may be usable multiple times by being subjected to cleaning-disinfecting treatment.

In the aforementioned embodiment, the wire connection portion 94 of the treatment tool elevator 36 has a shape projecting further on the X(+) direction side than the elevator main body portion 90. The wire connection portion 94, however, may be formed to be a substantially planar shape at a side surface on the X(+) direction side of the elevator distal end portion 92 (refer to JP-H05-56913 and JP-H06-315458 mentioned above). Also in this case, due to the second wall surface 102 and the step surface 104, the treatment tool tip portion is prevented from slipping into the Z(−) direction side of the wire distal end portion 38*a* positioned on the X(+) direction side with respect to the elevator main body portion 90.

In the aforementioned embodiment, a side-viewing endoscope (duodenoscope) has been described as an example of the endoscope 10. The present invention is, however, applicable to various types of endoscopes, such as ultrasonic endoscope, that change the orientation of the treatment tool elevator 36 by the wire pulling method and to a treatment tool elevating mechanism thereof.

Ultrasonic Endoscope

Next, an ultrasonic endoscope 300 (refer to FIG. 16) to which the present invention is applied and a treatment tool elevating mechanism thereof will be described. Components whose functions or configurations are the same as those of the endoscope 10 (side-viewing endoscope) in the aforementioned embodiment are given the same signs, and description thereof is omitted. Configurations of the ultrasonic endoscope 300 other than an insertion-section distal end portion 302 of the insertion section 24 are publicly known technologies, and thus, specific description thereof is omitted here.

Figure 16:
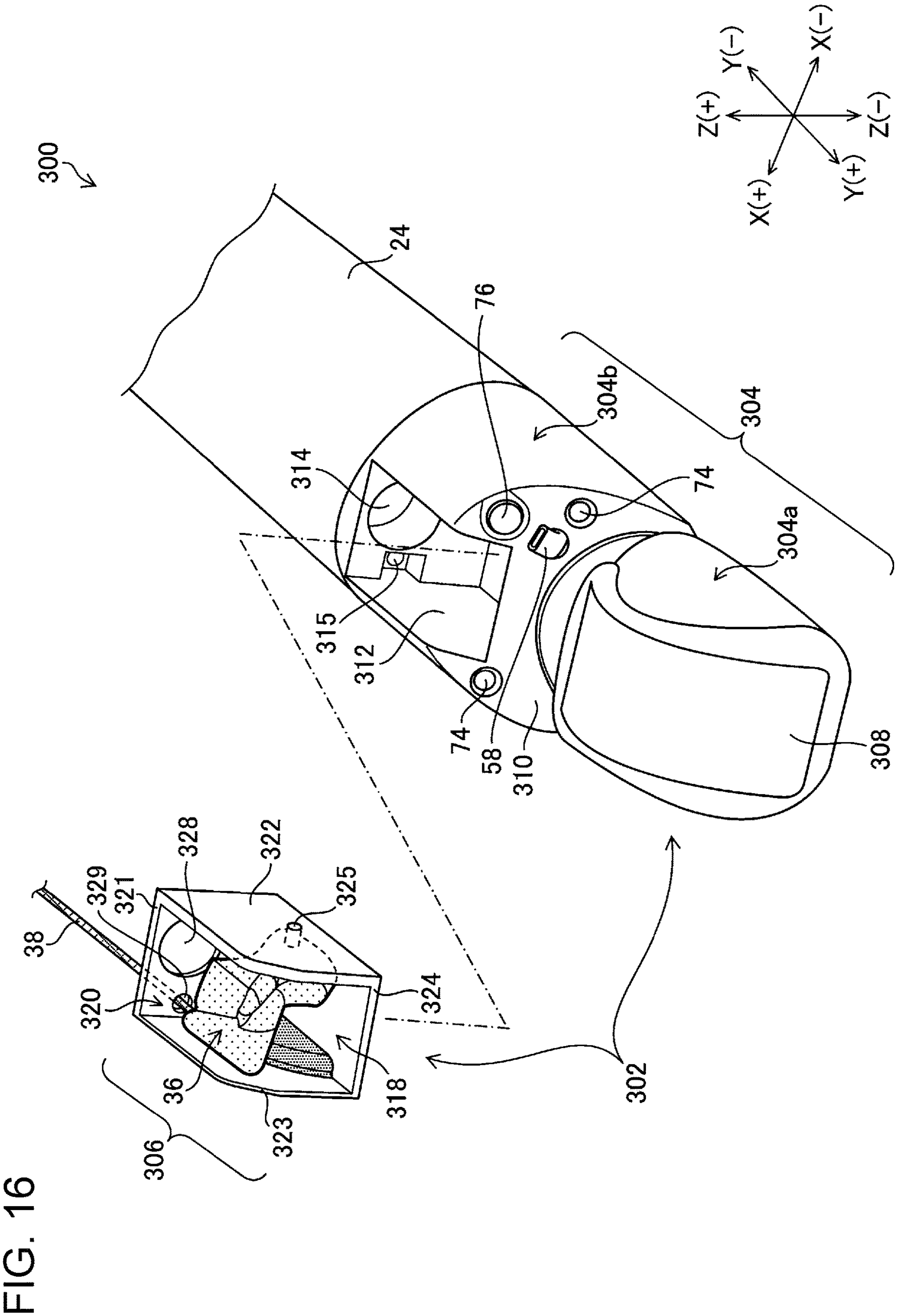
FIG. 16 is an exploded perspective view of an insertion-section distal end portion of an ultrasonic endoscope.

FIG. 16 is an exploded perspective view of the insertion-section distal end portion 302 of the ultrasonic endoscope 300. As illustrated in FIG. 16, the insertion-section distal end portion 302 includes a distal-end-portion main body 304 (also referred to as the hard tip portion) and an elevator unit 306 detachably attached to the distal-end-portion main body 304.

The distal-end-portion main body 304 includes a transducer attaching portion 304*a* and a main-body base portion 304*b* in the order from the Y(+) direction side toward the Y(−) direction side.

An ultrasonic transducer 308 is attached to the transducer attaching portion 304*a*. Although illustration is omitted, a balloon that covers and encloses the ultrasonic transducer 308 can be detachably mounted on the transducer attaching portion 304*a*.

The ultrasonic transducer 308 is of a convex type having an ultrasonic wave transmission-reception surface at which a large number of ultrasonic vibrators that transmit and receive ultrasonic waves are arranged. The structure and the function of the ultrasonic transducer 308 are publicly known technologies, and thus, specific description thereof is omitted here.

At the main-body base portion 304*b*, an inclined surface 310 and an elevator-unit attaching hole 312 are provided in the order from the Y(+) direction side toward the Y(−) direction side.

When viewed from the X direction side, the inclined surface 310 is gradually inclined downward from the Y(−) direction side toward the Y(+) direction side. The inclined surface 310 is provided with the illumination window 74, the observation window 76, and the air/water supply nozzle 58, which are mentioned above.

The elevator-unit attaching hole 312 is a rectangular hole that opens at a surface of the main-body base portion 304*b* on the Z(+) direction side. The elevator unit 306, which will be described later, is detachably attached to the elevator-unit attaching hole 312. A treatment-tool insertion port 314 connected to the aforementioned treatment tool channel 37, and a wire insertion hole 315 connected to the aforementioned wire channel 40 are formed at, in wall surfaces that constitute the elevator-unit attaching hole 312, a wall surface that defines the Y(−) direction side of the elevator-unit attaching hole 312.

Figure 17:
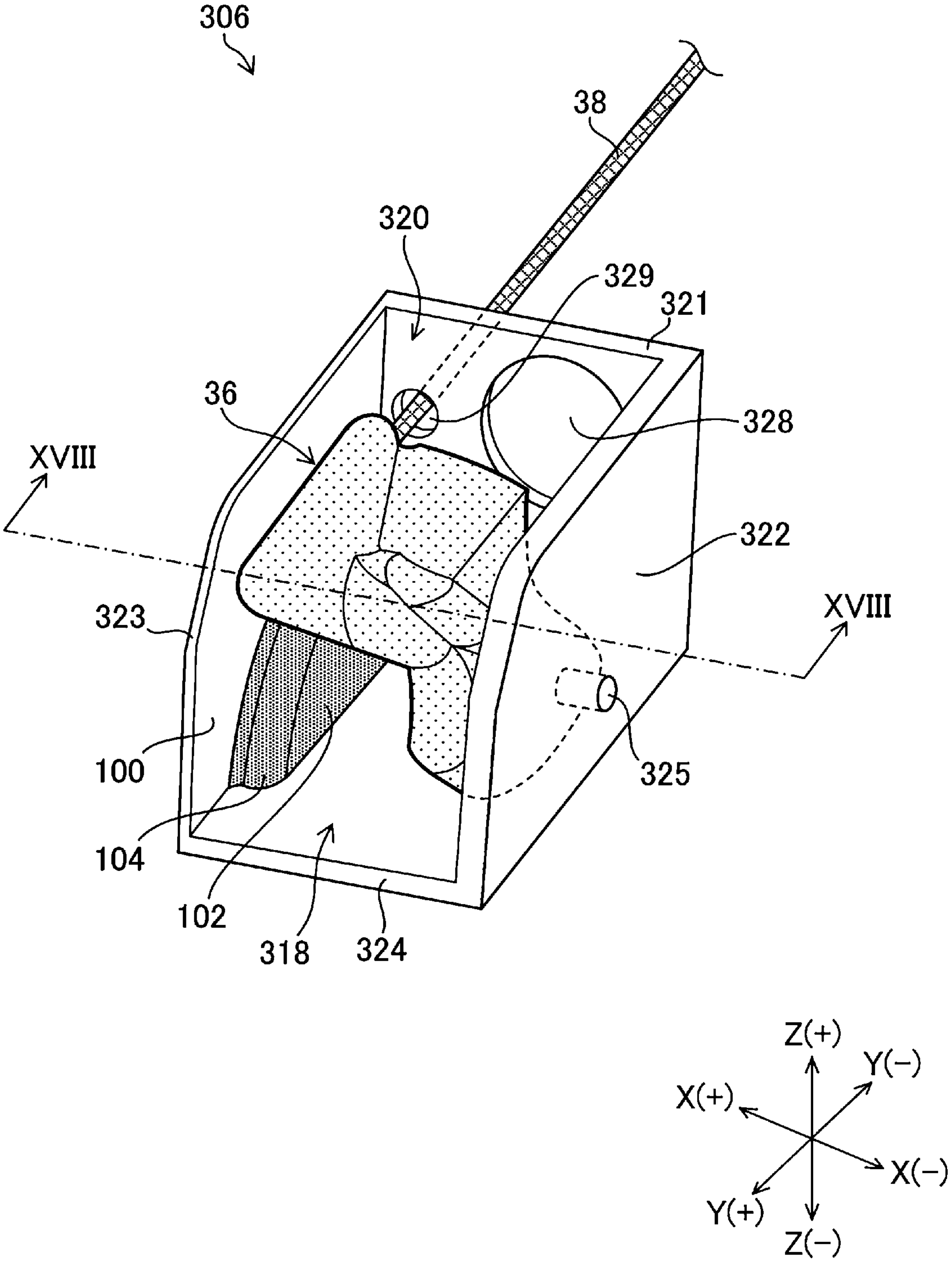
FIG. 17 is an enlarged perspective view of an elevator unit.

FIG. 17 is an enlarged perspective view of the elevator unit 306. As illustrated in FIG. 17 and aforementioned FIG. 16, the elevator unit 306 corresponds to the elevator-housing-space forming member in the present invention. The elevator unit 306 has an elevator housing space 318 and rotatably holds the aforementioned treatment tool elevator 36. The elevator unit 306 is detachably mounted on the elevator-unit attaching hole 312. The elevator unit 306, the treatment tool elevator 36, and the operating wire 38 constitute the treatment tool elevating mechanism in the present invention. The elevator unit 306, the treatment tool elevator 36, and the operating wire 38 are disposable items (replaceable items) that are detached from the distal-end-portion main body 304 after completion of the use of the ultrasonic endoscope 300 and discarded.

The elevator unit 306 has an opening portion 320, a proximal end wall portion 321, a first wall portion 322, a second wall portion 323, a bottom wall portion 324, and a rotary shaft 325. The proximal end wall portion 321, the first wall portion 322, the second wall portion 323, and the bottom wall portion 324 form the elevator housing space 318.

The opening portion 320 exposes the elevator housing space 318 when the elevator unit 306 (distal-end-portion main body 304) is viewed from the Z(+) direction side thereof. Consequently, it is possible to lead out a treatment tool from the elevator housing space 318 to the Z(+) direction side.

The proximal end wall portion 321 defines the Y(−) direction side of the elevator housing space 318. A treatment tool lead-out port 328 and a wire insertion hole 329 open at the proximal end wall portion 321.

When the elevator unit 306 is mounted on the elevator-unit attaching hole 312, the treatment tool lead-out port 328 is connected to the treatment tool channel 37 via the treatment-tool insertion port 314. Consequently, a treatment tool is led out to the outside through the treatment tool lead-out port 328 via the elevator housing space 318 (treatment tool elevator 36). When the elevator unit 306 is mounted on the elevator-unit attaching hole 312, the wire insertion hole 329 is connected to the wire channel 40 via the wire insertion hole 315. Consequently, it is possible to insert the operating wire 38 into the wire channel 40 through the wire insertion hole 329 via the wire insertion hole 315.

The first wall portion 322 is provided, on the distal end surface side of the proximal end wall portion 321, at a position on the X(−) direction side with respect to the treatment tool lead-out port 328, and has a shape extending on the Y(+) direction side. The first wall portion 322 defines the X(−) direction side of the elevator housing space 318.

The second wall portion 323 is provided, on the distal end surface side of the proximal end wall portion 321, at a position on the X(+) direction side with respect to the treatment tool lead-out port 328, and has a shape extending on the Y(+) direction side. The second wall portion 323 defines the X(+) direction side of the elevator housing space 318. Consequently, the width of the elevator housing space 318 in the X direction is defined by the first wall portion 322 and the second wall portion 323. At a surface of the second wall portion 323 on the side facing the first wall portion 322, that is, on the X(−) direction side, the first wall surface 100, the second wall surface 102, and the step surface 104 similar to those in the aforementioned embodiment (refer to FIG. 7) are formed.

When the elevator unit 306 is viewed from the Z(−) direction side, the bottom wall portion 324 is provided between end portions on the Z(−) direction side of the two of the first wall portion 322 and the second wall portion 323 so as to cover the elevator housing space 318. The bottom wall portion 324 defines the Z(−) direction side of the elevator housing space 318.

The rotary shaft 325 is basically the same as the rotary shaft 88 in the aforementioned embodiment, and has one end attached to the first wall portion 322 and another end attached to the second wall portion 323. The rotary shaft 325 holds the treatment tool elevator 36 so as to be rotatable between the lying position and the elevated position (refer to FIG. 12).

Figure 18:
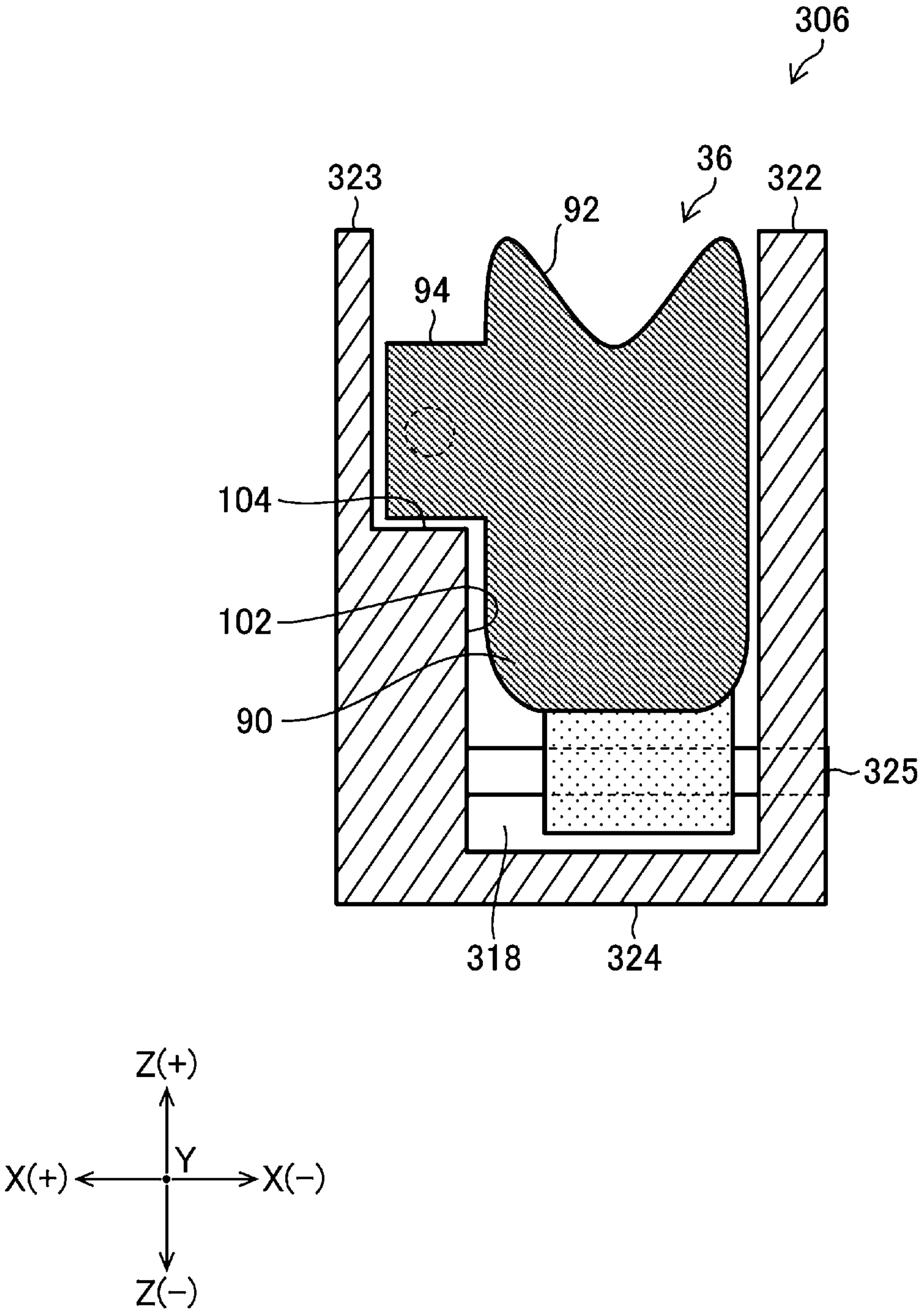
FIG. 18 is a sectional view along line XVIII-XVIII in FIG. 17.

FIG. 18 is a sectional view along line XVIII-XVIII in FIG. 17. In FIG. 18, the treatment tool elevator 36 is simply illustrated. As illustrated in FIG. 18, the treatment tool elevator 36 includes the elevator main body portion 90, the elevator distal end portion 92, and the wire connection portion 94, which are described above.

When the insertion-section distal end portion 302 (elevator unit 306) is viewed from the Z(+) direction side, the second wall surface 102 overlaps at least a portion of the wire connection portion 94 (wire distal end portion 38*a*; refer to FIG. 9) in the X direction. Therefore, as with the aforementioned embodiment, the second wall surface 102 prevents the treatment tool tip portion from slipping into a gap on the Z(−) direction side of the wire distal end portion 38*a*.

As with the aforementioned embodiment, the step surface 104 prevents, together with the second wall surface 102, the treatment tool tip portion from slipping into the gap on the Z(−) direction side of the wire distal end portion 38*a*. The step surface 104 functions as a guide surface of the wire distal end portion 38*a* when the treatment tool elevator 36 rotates between the lying position and the elevated position.

As described above, by forming the second wall surface 102 and the step surface 104 at the second wall portion 323 of the elevator unit 306, it is possible to prevent the treatment tool tip portion from slipping into a position on the Z(−) direction side of the wire distal end portion 38*a*. In addition, since providing the second wall portion 323 (the second wall surface 102 and the step surface 104) at the disposable-type elevator unit 306 eliminates the need to provide a configuration corresponding to the second wall portion 323 at the distal-end-portion main body 304, accessibility of a cleaning brush with respect to the distal-end-portion main body 304 after the elevator unit 306 is detached is prevented from being degraded. Further, even when the step surface 104 is worn by sliding with the wire distal end portion 38*a*, there is no problem since the elevator unit 306 is discarded every time when the use of the ultrasonic endoscope 300 is completed. As a result, it is possible to achieve improvement in accessibility of a cleaning brush, prevention of wear of the distal-end-portion main body 304, and prevention of a treatment tool from slipping into the Z(−) direction side of the operating wire 38.

REFERENCE SIGNS LIST

10 endoscope
12 endoscope system
14 endoscopic processor device
15 light source device

15A processor-side connector
16 image processing device
18 display
20 elevation operation lever
22 operation section
24 insertion section
26 soft portion
28 bending portion
30 insertion-section distal end portion
32 distal-end-portion main body
34 cap
36 treatment tool elevator
36*a* treatment tool guide surface
37 treatment tool channel
38 operating wire
38*a* wire distal end portion
40 wire channel
42 air/water supply tube
44 cable insertion channel
46 operation-section main body
48 grip portion
50 bend stopper tube
52 universal cable
54 connector device
57 air/water supply button
58 air/water supply nozzle
59 suction button
60 treatment tool lead-out port
61 wire insertion hole
62 angle knob
64 treatment tool lead-in port
65 proximal end wall portion
66 elevator housing space
68 first wall portion
74 illumination window
76 observation window
80 first opening window
82 cap distal end portion
82*a* second opening window
84 elevator holding portion
86 second wall portion
88 rotary shaft
90 elevator main body portion
90*a* insertion hole
92 elevator distal end portion
94 wire connection portion
96 wire attaching portion
100 first wall surface
102 second wall surface
104 step surface
200 first metal mold
202 second metal mold
204 through hole
210 first metal mold
210*a* mold surface
212 second metal mold
300 ultrasonic endoscope
302 insertion-section distal end portion
304 distal-end-portion main body
304*a* transducer attaching portion
304*b* main-body base portion
306 elevator unit
308 ultrasonic transducer
310 inclined surface
312 elevator-unit attaching hole
314 treatment-tool insertion port
315 wire insertion hole

318 elevator housing space
320 opening portion
321 proximal end wall portion
322 first wall portion
323 second wall portion
324 bottom portion
325 rotary shaft
328 treatment tool lead-out port
329 wire insertion hole
Ax long axis direction
CA center axis

What is claimed is:

1. An endoscope comprising:
an operation section at which an operating member is provided;
an insertion section that is provided on a distal end side of the operation section and that is to be inserted into a subject;
a distal-end-portion main body that is positioned at a distal end of the insertion section;
an elevator-housing-space forming member that is detachably attached to the distal-end-portion main body and that forms an elevator housing space;
a proximal end wall portion that is provided at the distal-end-portion main body or the elevator-housing-space forming member and at which a lead-out port for a treatment tool opens;
a first wall portion that extends from the proximal end wall portion to a distal end side of the distal-end-portion main body, the first wall portion being provided at a position on one direction side of a first direction perpendicular to a longitudinal axis of the distal-end-portion main body with respect to the lead-out port;
a second wall portion that is provided at the elevator-housing-space forming member and that forms, together with the proximal end wall portion and the first wall portion, the elevator housing space, the second wall portion facing the first wall portion at a position on another direction side opposite to the one direction side with respect to the lead-out port;
a treatment tool elevator that is disposed in the elevator housing space and that is rotatable between a lying position and an elevated position about a rotary shaft parallel to the first direction, the treatment tool elevator having an elevator main body portion rotatably held by the rotary shaft, an elevator distal end portion provided on a distal end side of the elevator main body portion, and a wire connection portion provided at the elevator distal end portion; and
an operating wire that is connected to the wire connection portion and that rotates the treatment tool elevator,
wherein, when viewed in a second direction perpendicular to both the longitudinal axis and the first direction, a wire distal end portion of the operating wire connected to the wire connection portion is positioned on the another direction side with respect to the elevator main body portion,
wherein the second wall portion has:
a first wall surface facing the first wall portion at least a portion of which has a shape along a trajectory of the wire connection portion that rotates about the rotary shaft; and
a second wall surface facing the first wall portion that is provided at a position on the one direction side with respect to the first wall surface and that has a shape extending along a trajectory of the elevator main body portion that rotates about the rotary shaft,
wherein a curvature of the operating wire is substantially similar to a curvature of the second wall surface, and
wherein the second wall surface overlaps at least a portion of the wire distal end portion in the first direction when viewed in the second direction.

2. The endoscope according to claim 1, wherein the wire distal end portion has a shape projecting further from the elevator distal end portion on the other direction side than the elevator main body portion.

3. The endoscope according to claim 1, wherein the second wall surface is provided at a position on the one direction side with respect to a center axis of the wire distal end portion when viewed in the second direction.

4. The endoscope according to claim 1,
wherein the second wall portion has a step surface formed between the first wall surface and the second wall surface, and
wherein the step surface has a shape extending along a trajectory of the wire distal end portion that rotates about the rotary shaft.

5. The endoscope according to claim 4, wherein the step surface has an arc shape when viewed in the first direction.

6. The endoscope according to claim 1, wherein the first wall surface is provided on the other direction side with respect to the operating wire when viewed in the second direction.

7. The endoscope according to claim 1,
wherein the distal-end-portion main body has the proximal end wall portion and the first wall portion, and
wherein the elevator-housing-space forming member is a cap having the second wall portion.

8. The endoscope according to claim 7, wherein an opening window that exposes the elevator housing space when viewed from a distal end side of the cap is formed at a distal end portion of the cap.

9. The endoscope according to claim 1,
wherein the elevator-housing-space forming member has the proximal end wall portion, the first wall portion, and the second wall portion, and
wherein the endoscope comprises an ultrasonic transducer provided on a distal end side of the distal-end-portion main body.

10. The endoscope according to claim 1, comprising an insert molded body in which the treatment tool elevator and the operating wire are integrated with each other.

11. The endoscope according to claim 1, wherein the treatment tool elevator and the operating wire are formed as separate bodies.

12. A treatment tool elevating mechanism that is to be attached to a distal-end-portion main body of an endoscope and that changes a lead-out direction of a treatment tool, the endoscope comprising
an operation section at which an operating member is provided,
an insertion section that is provided on a distal end side of the operation section and that is to be inserted into a subject, and
the distal-end-portion main body that is positioned at a distal end of the insertion section,
the treatment tool elevating mechanism comprising:
an elevator-housing-space forming member that is detachably attached to the distal-end-portion main body and that forms an elevator housing space;
a proximal end wall portion that is provided at the distal-end-portion main body or the elevator-housing-space forming member and at which a lead-out port for the treatment tool opens;

a first wall portion that extends from the proximal end wall portion to a distal end side of the distal-end-portion main body, the first wall portion being provided at a position on one direction side of a first direction perpendicular to a longitudinal axis of the distal-end-portion main body with respect to the lead-out port;

a second wall portion that is provided at the elevator-housing-space forming member and that forms, together with the proximal end wall portion and the first wall portion, the elevator housing space, the second wall portion facing the first wall portion at a position on another direction side opposite to the one direction side with respect to the lead-out port;

a treatment tool elevator that is disposed in the elevator housing space and that is rotatable between a lying position and an elevated position about a rotary shaft parallel to the first direction, the treatment tool elevator having an elevator main body portion rotatably held by the rotary shaft, an elevator distal end portion provided on a distal end side of the elevator main body portion, and a wire connection portion provided at the elevator distal end portion; and an operating wire that is connected to the wire connection portion and that rotates the treatment tool elevator, wherein, when viewed in a second direction perpendicular to both the longitudinal axis and the first direction, a wire distal end portion of the operating wire connected to the wire connection portion is positioned on the another direction side with respect to the elevator main body portion, wherein the second wall portion has:

a first wall surface facing the first wall portion at least a portion of which has a shape along a trajectory of the wire connection portion that rotates about the rotary shaft; and a second wall surface facing the first wall portion that is provided at a position on the one direction side with respect to the first wall surface and that has a shape extending along a trajectory of the elevator main body portion that rotates about the rotary shaft, wherein a curvature of the operating wire is substantially similar to a curvature of the second wall surface, and wherein the second wall surface overlaps at least a portion of the wire distal end portion in the first direction when viewed in the second direction.

13. The treatment tool elevating mechanism according to claim 12, wherein the second wall surface is provided at a position on the one direction side with respect to a center axis of the wire distal end portion when viewed in the second direction.

* * * * *